United States Patent [19]

Gangjee

[11] Patent Number: 5,736,547

[45] Date of Patent: *Apr. 7, 1998

[54] DERIVATIVES OF PYRIDO [2,3-D] AND [3,2-D] PYRIMIDINE AND QUINAZOLINE AND METHOD OF USING THESE DERIVATIVES

[75] Inventor: Aleem Gangjee, Allison Park, Pa.

[73] Assignee: Duquesne University of the Holy Ghost, Pittsburgh, Pa.

[*] Notice: The portion of the term of this patent subsequent to Sep. 12, 2014, has been disclaimed.

[21] Appl. No.: 515,491

[22] Filed: Aug. 15, 1995

Related U.S. Application Data

[60] Division of Ser. No. 304,044, Sep. 12, 1994, Pat. No. 5,508,281, which is a continuation-in-part of Ser. No. 950,982, Sep. 23, 1992, Pat. No. 5,346,900, which is a continuation of Ser. No. 829,519, Jan. 31, 1992, abandoned, which is a continuation of Ser. No. 682,043, Apr. 8, 1991, abandoned.

[51] Int. Cl.$^6$ ............... A61K 31/505; C07D 471/04
[52] U.S. Cl. .......................... 514/258; 544/279
[58] Field of Search ............... 544/279; 514/258

[56] References Cited

U.S. PATENT DOCUMENTS

| | | | |
|---|---|---|---|
| 3,904,624 | 9/1975 | Perronnet et al. | 260/251 A |
| 5,346,900 | 9/1994 | Gangjee | 514/258 |

OTHER PUBLICATIONS

Werbel et al., J. Heterocyclic Cheun., 24, 345 1987.

"Studies on Condensed Pyrimidine Systems. XXIII. Synthesis of 2,4-Diaminopyrido [2,3-d]pyrimidines from B-Keto Esters". *J. Med. Chem.*, vol. 11, pp. 703-707 (1968), B. S. Hurlbert et al.

"Studies on Condensed Pyrimidine Systems. XXIV. The Condensation of 2,4,6-triaminopyrimidine with Malondialdehyde Derivatives"*J. Med. Chem.*, vol. 11, pp. 708-710 (1968), B. S. Hurlbert et al.

"Studies on Condensed Pyrimidine Systems. XXV. 2,4-Diaminopyrido [2,3-d]pyrimidines. Biological Data", *J. Med. Chem*, vol. 11, pp. 711-717 (1968), B. S. Hurlbert et al.

"Synthesis and Antitumor Activity of 2,4-Diamino-6-(2,5-dimethoxybenzyl)-5-methylpyrido[2,3-d]pyrimidine", *J. Med. Chem.*, vol. 23, pp. 327-329 (1980), E. M. Grivsky et al.

"Folate Antagonists. 20. Synthesis and Antitumor and Antimalarial Properties of Trimetrexate and Related 6-[(Phenylamino)methyl]-2,4-quinazolinediamines", *J. Med. Chem.*, vol. 26, pp. 1753-1760 (1983), E. F. Elslager et al.

"Synthesis and Antifolate Activity of 5-Methyl-5-deaza Analogues of Aminopterin, Methotrexate, Folic Acid, and N$^{10}$-Methylfolic Acid", *J. Med. Chem.*, vol. 29, pp. 1080-1087 (1986), J. B. Piper et al.

"Synthesis and Antimalarial Activity of a Series of 2,4-Diamino-6-[(N-alkylanilino)methyl]quinazolines [1,2], *J. Heterocyclic Chem.*, vol. 24, pp. 345-349 (1987), Leslie M. Werbel et al.

*Primary Examiner*—Mukund J. Shah
*Assistant Examiner*—Pavanaram K. Sripada
*Attorney, Agent, or Firm*—Arnold B. Silverman; Diane R. Meyers; Eckert Seamans Cherin & Mellott, LLC

[57] ABSTRACT

The invention discloses species compounds (4) and (5) and methods of using these compounds for therapeutically treating a patient for an illness selected from the group consisting of infection by *Pneumocystis carinii* and *Toxoplasmosis gondii*.

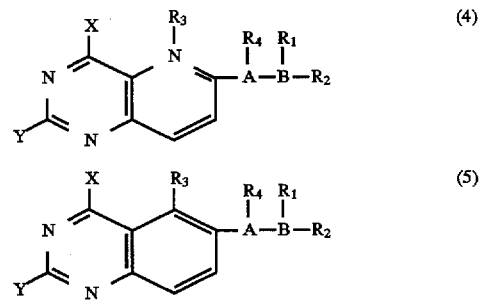

In compounds (4) and (5) X and Y may be the same or different and are selected from the group consisting of OH and $NH_2$: A is selected from the group consisting of nitrogan, carbon and sulfur and B equals carbon when A is selected from the group consisting of sulfur, carbon and nitrogen, B equals nitrogen when A equals carbon and B equals sulfur when A equals carbon; $R_3$ is one of either hydrogen or methyl except when attached to Nitrogen wherein $R_3$ is zero; $R_4$ is one of either a hydrogen or a first lower alkyl group except when A equals sulfur wherein $R_4$ is zero; $R_1$ is selected from the group consisting of hydrogen, nitroso group, aldehyde, a second lower alkyl group except when B is equal to sulfur wherein $R_1$ is zero; and $R_2$ is selected from the group consisting alkyl, dialkyl and trialkyl groups, alkylaryl, diaryl and triaryl groups, substituted aryl, diaryl and triaryl groups, an alkoxy, substituted alkoxy and halogen.

16 Claims, 2 Drawing Sheets

DERIVATIVES OF PYRIDO [2,3-D] AND [3,2-D] PYRIMIDINE AND QUINAZOLINE AND METHOD OF USING THESE DERIVATIVES

This is a division of application Ser. No. 08/304,044, filed Sep. 12, 1994, now patented U.S. Pat. No. 5,505,281 which is a continuation-in-part application of U.S. application Ser. No. 07/950,982 filed Sep. 23, 1992 now U.S. Pat. No. 5,346,900 which is a continuation of U.S. application Ser. No. 07/829,519 filed Jan. 31, 1992, now abandoned, which is a continuation of U.S. application Ser. No. 07/682,043 filed Apr. 8, 1991, now abandoned. The invention described herein was made in the course of work supported in part by the National Institutes of General Medical Sciences, Grant No. 1-RO1-GM-40998 from the National Institutes of Health, U.S. Department of Health and Human Services. The Government has certain rights in this invention.

BACKGROUND OF THE INVENTION

1. Field of the Invention

This invention relates to 5-alkyl-6-[[amino]methyl]pyrido[2,3-d]pyrimidine compounds and pharmaceutically acceptable salts thereof. More specifically, it relates to compounds useful in resisting *Pneumocystis carinii* and *Toxoplasmosis gondii* infections in immunocompromised patients, such as, for example, patients with autoimmune deficiency syndrome (AIDS). These compounds are useful, for example, as potential antitumor, antibiotic, antimalarial, antifungal or antiprotozoal agents or as synergistic agents with sulfonamides and may require the use of leucovorin rescue. Methods of preparing and using these compounds are also provided. It also relates to derivatives of pyrido[2,3-d] and [3,2-d] pyrimidine and quinazoline compounds and pharmaceutically acceptable salts thereof.

2. Description of the Prior Art

The pyrido[2,3-d]pyrimidine ring system has been studied due to its involvement in the inhibition of dihydrofolate reductase (DHFR) enzymes activity. The pyrido [2,3-d] pyrimidine derivatives inhibit the normal cell growth of a variety of cells. Methotrexate (MTX), trimetrexate (TMX) and piritrexim and other folic acid analogues function as inhibitors of cell growth by similar mechanisms involving the inhibition of dihydrofolate reductase. Inhibition of dihydrofolate reductase deprives the cell of 5,10-methylenetetrahydrofolate. 5,10-methylenetetrahydrofolate is essential for cell growth. Dihydrofolate reductase reduces dihydrofolate to tetrahydrofolate. The inhibition of dihydrofolate reductase by the compounds and pharmaceutically acceptable salts of this invention results in the inhibition of DNA synthesis and leads to cell death.

Elslager, Edward F., et al., "Folate Antagonists. 20. Synthesis and Antitumor and Antimalarial Properties of Trimetrexate and Related 6-[(Phenylamino)methyl]-2,4-quinazolinediamines" *J. Med. Chem.*, Vol. 26 pp. 1753–1760 (1983)), discloses the preparation of quinazolinediamines. This article states that the quinazolinediamines exhibit potent antimalarial, antibacterial and antitumor activity.

Methods to synthesize diaminopyrido[2,3-d]pyrimidines having various substituents are known. See Hurlbert, B. S., et al., "Studies on Condensed Pyrimidine Systems. XXIII. Synthesis of 2,4-Diaminopyrido[2,3-d]pyrimidines from β-Keto Esters", *J. Med. Chem.*, Vol. 11, pp. 703–707 (1968), and Hurlbert, B. S., and Valenti, B. F., "Studies on Condensed Pyrimidine Systems. XXIV. The Condensation of 2,4,6-Tfiaminopyridimine with Malondialdehyde Derivatives", *J. Med. Chem.*, Vol. 11, pp. 708–710 (1968).

Hurlbert, B. S., et al., "Studies on Condensed Pyrimidine Systems. XXV. 2,4-Diaminopyrido[2,3-d]pyrimidines. Biological Dam", *J. Med. Chem.*, Vol. 11, pp. 711–717 (1968), discloses the antimicrobial activities of several subgroups of pyridopyrimidines. This article states that 2,4-diaminopyrido[2,3-d]pyrimidines bearing alkyl and aralkyl substituents in the pyrimidine moiety are inhibitors of dihydrofolate reductase having antibacterial and antiprotozoal activity and that these compounds potentiate sulfonamides.

Grivsky, E. M., et al., "Synthesis and Antitumor Activity of 2,4-Diamino-6-(2,5-dimethoxybenzyl)-5-methylpyrido[2,3-d]pyridimine", *J. Med. Chem.*, Vol. 23, pp. 327–329 (1980), discloses the synthesis of 2,4-diamino-6-(2,5-dimethoxybenzyl)-5-methylpyrido[2,3-d]pyfidimine (BW301U,7). This article states ihat BW301U,7 is as effective as methotrexate as an inhibitor of dihydrofolate reductase purified from human leukemic cells and, in contrast to metoprine, has minimal activity as an inhibitor of histamine metabolism.

Werbel, Leslie, M., et al., "Synthesis and Antimalarial Activity of a Series of 2,4-Diamino-6-[(N-alkylanilino) methyl]quinazolines [1,2]", *J. Heterocyclic Chem.*, Vol. 24, pp. 345–349 (1987), discloses the synthesis of N6 substituted quinazoline dihydrofolate reductase inhibitors. This article states that these analogs demonstrate substantial activity against *Plasmodium berghei* infections in mice.

Piper, J. R., et al., "Syntheses and Antifolate Activity of 5-Methyl-5-deaza Analogues of Aminopterin, Methotrexate, Folic Acid, and $N^{10}$-Methylfolic Acid", *J. Med. Chem.*, Vol. 29, pp. 1080–1087 (1986), discloses that 5-methyl-5-deaza analogues of aminopterin and methotrexate are much more growth inhibitory than methotrexate.

In spite of the prior art disclosures, there remains a very real and substantial need for an inhibitor of dihydrofolate reductase that is more active and more selective than known compounds having antitumor, antibiotic, antimalarial, antifungal or antiprotozoal activity or as synergistic agents with sulfonamides, and for methods of preparing and using such compounds.

SUMMARY OF THE INVENTION

The present invention has met the hereinbefore described need. The present invention provides compounds and pharmaceutically acceptable salts having a general formula (1):

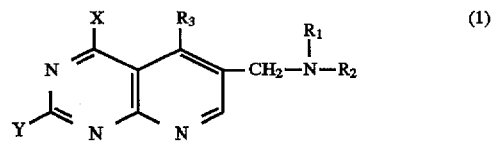

wherein X and Y may be the same or different and are selected from the group consisting of OH and $NH_2$; wherein $R_1$ is selected from the group consisting of hydrogen, a first lower alkyl group, a nitroso group and an aldehyde; and wherein $R_2$ is selected from the group consisting of a second lower alkyl group which is the same as or different than the first lower alkyl group, an aryl group, an alkylaryl group, a substituted aryl group and a substituted alkylaryl group, and each substituent of the substituted aryl group or the substituted alkylaryl group is the same or different and is selected from the group consisting of a third lower alkyl group which is the same as or different than the first lower alkyl group or the second lower alkyl group, an aikoxy group, a substituted alkoxyaryloxy group, and a halogen; and wherein R₃ is a fourth lower alkyl group which is the same as or different than the first lower alkyl group, the second lower alkyl group or the third lower alkyl group.

The present invention also provides compounds and pharmaceutically acceptable salts having the generic formula (2):

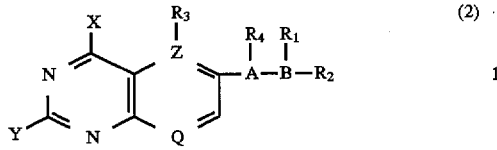

wherein X and Y may be the same or different and are selected from the group consisting of OH and NH₂; wherein Z is one of either nitrogen or carbon and Q is one of either nitrogen or carbon but when Z equal nitrogen, Q does not equal nitrogen and when Q equal nitrogen, Z does not equal nitrogen; wherein A is selected from the group consisting of nitrogen, carbon and sulfur and B equals carbon when A is selected from the group consisting of sulfur, carbon, and nitrogen, B equal nitrogen when A equal carbon and B equals sulfur when A equals carbon; wherein R₃ is one of either hydrogen or methyl except where Z is nitrogen wherein R₃ zero; wherein R₄ is one of either a H or a first lower alkyl group except when A equals sulfur wherein R₄ is zero; wherein R₁ is selected from the group consisting of a hydrogen, a nitroso group, an aldehyde, a second lower alkyl group which is the same or different than the first lower alkyl group except when B is equal to sulfur wherein R₁ zero; and wherein R₂ is selected from the group consisting of a third lower alkyl group which is the same or different than the first lower and the second lower alkyl groups, an aryl group, an alkylaryl group, a substituted aryl group, a substituted alkylaryl group, a diaryl group, a triaryl group, an alkyldiaryl group, an alkyltriaryl group, a substituted diaryl group and a substituted triaryl group, and each substituent of the substituted aryl group, diaryl group, triaryl group or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group, and a halogen.

The first species of the generic structure shown in (2) is the compounds and pharmaceutically acceptable salts having the formula (3):

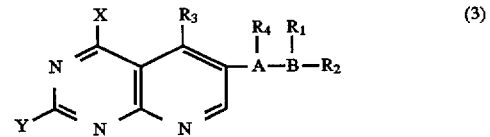

wherein X and Y may be the same or different and are selected from the group consisting of OH and NH₂; wherein A is selected from the group consisting of nitrogen, carbon and sulfur and B equals carbon when A is selected from the group consisting of sulfur, carbon and nitrogen or B equals nitrogen when A equals carbon and B equals sulfur when A equals carbon; wherein R₃ is one of either hydrogen or methyl; wherein R₄ is one of either H or a first lower alkyl group except where A equals sulfur wherein R₄ is zero; wherein R₁ is selected from the group consisting of hydrogen, a nitroso group, an aldehyde, a second lower alkyl group which is the same or different from the first lower alkyl group; except when B is equal to sulfur wherein R₁ is zero; and wherein R₂ is selected from the group consisting of a third lower alkyl group which is the same or different than the first lower alkyl group, and the second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group and a substituted triaryl group, and each substituent of the substituted aryl group, diaryl group, and triaryl group or the substituted alkylaryl group, alkyldiaryl group and alkyltriaryl group is the same or different and is selected from the group consisting of a fourth lower alkyl group which is the same as or different from the first lower alkyl group, the second lower alkyl group, the third lower alkyl group, an alkoxy, a substituted alkoxyaryloxy group and a halogen.

The second species of the generic structure shown in (2) is the compounds and pharmaceutically acceptable salts having the formula (4):

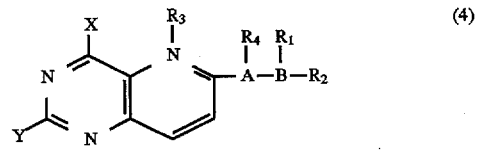

wherein X and Y may be the same or different and are selected from the group consisting of OH and NH₂; wherein A is selected from the group consisting of nitrogen, carbon and sulfur and B equals carbon when A is selected from the group consisting of sulfur, carbon and nitrogen or B equals nitrogen when A equals carbon or B equals sulfur when A equals carbon wherein R₃ is zero; wherein R₄ is one of either a hydrogen or a first lower alkyl group except where A equals sulfur wherein R₄ is zero; wherein R₁ is selected from the group consisting of hydrogen, a nitroso group, an aldehyde, a second lower alkyl group which is the same or different than the first lower alkyl group except when B is equal to sulfur wherein R₁ is zero; and wherein R₂ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group, and a substituted triaryl group, and each substituent of the substituted aryl group, diaryl group, triaryl group or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group, and a halogen.

The third species of the generic structure shown in (2) is the compounds and pharmaceutically acceptable salts having the formula (5):

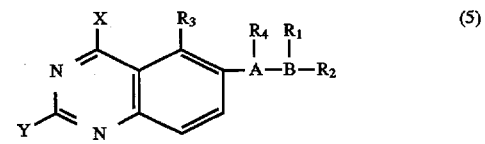

wherein X and Y may be the same or different and are selected from the group consisting of OH and NH₂; wherein A is selected from the group consisting of nitrogen, carbon and sulfur and B equals carbon when A is selected from the group consisting of sulfur, carbon and nitrogen or B equals nitrogen when A equals carbon or B equals sulfur when A equals carbon; wherein $R_3$ is one of either hydrogen or methyl; wherein $R_4$ is one of either a hydrogen or a first lower alkyl group except where A equals sulfur wherein $R_4$ is zero; wherein $R_1$ is selected from the group consisting of hydrogen, a nitroso group, an aldehyde, a second lower alkyl group which is the same or different than the first lower alkyl group except when B is equal to sulfur wherein $R_1$ is zero; and wherein $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group, and a substituted triaryl group, and each substituent of the substituted aryl group, diaryl group, triaryl group or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group, and a halogen.

The present invention also provides compounds and pharmaceutically acceptable salts having a general formula (6):

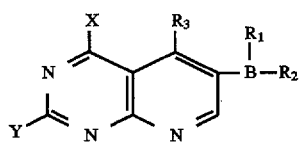

(6)

wherein X and Y may be the same or different and are selected from the group consisting of OH and $NH_2$; wherein B is selected from the group consisting of nitrogen, carbon, sulfur and oxygen; wherein $R_3$ is one of either hydrogen or methyl; wherein $R_1$ is selected from the group consisting of hydrogen, a nitroso group, an aldehyde, a first lower alkyl group except when B is one of either sulfur or oxygen wherein $R_1$ is zero; and wherein $R_2$ is selected from the group consisting of a second lower alkyl group which is the same or different than the first lower alkyl group, an aryl group, an alkylaryl group, a substituted aryl group, a substituted alkylaryl group, a diaryl group, a triaryl group, an alkyldiaryl group, an alkyltriaryl group, a substituted diaryl group and a substituted triaryl group and each substituent of the substituted aryl group, diaryl group, triaryl group or the substituted alkylaryl group, alkyldiaryl group and alkyltriaryl group is the same or different and is selected from the group consisting of a third lower alkyl group which is the same as or different from the first lower alkyl group, the second lower alkyl group, an alkoxy, a substituted alkoxyaryloxy group and a halogen.

In the generic compound 2, species compounds 3-5 and compound 6 and the pharmaceutically acceptable salts of these compounds, the first lower alkyl group has one to about six carbon atoms selected from the group consisting of branched, unbranched and acyclic, the second lower alkyl group has one to about six carbon atoms selected from the group consisting of branched, unbranched and acyclic; wherein the alkylaryl group is selected from the group consisting of an alkylphenyl and alkylbenzyl group; wherein the alkyldiaryl group is selected from the group consisting of alkylnaphthyl, alkylbenzothiophene, alkylindene, alkylbenzofuran, alkylindole and alkylaminoquinoline; wherein the alkyltriaryl group is an alkylanthracyl group; wherein the substituted aryl, diaryl and triaryl group is selected from the group consisting of a mono-, di- and tri-substituted alkylphenyl and alkylbenzyl group,
alkylnaphthyl, alkylbenzothiophene, alkylindole, alkylbenzofuran, alkylindene, alkylaminoquinoline, alkylanthracyl; wherein each substituted alkyldiaryl and alkyltriaryl group is selected from the group consisting of a mono-, di- and tri-substituted alkylnaphthyl, alkylbenzothiophene, alkylindole, alkylbenzofuran, alkylindene, alkylaminoquinoline and alkylanthracyl group; and wherein each substituent is the same or different and is selected from the group consisting of methyl, ethyl, n-propyl, n-butyl, branched n-pentyl, branched pentyl, n-hexyl, branched hexyl, cyclopropyl, cyclobutyl, cyclopentyl, cyclohexyl, methoxy group, chlorine atom, bromine atom and fluorine atom.

Pharmaceutically acceptable salts for FIGS. 1–6 include, for example, acetate, formate, glucuronate, ethantate or sulfonate.

In formulas 1–6, when X and Y are the same or different and are selected from the group consisting of OH and $NH_2$ groups, the enol form of the compounds is represented. The enol form is equivalent to and includes the keto form of the compounds.

This invention also provides a method for preparing the compounds and pharmaceutically acceptable salts described therein.

This invention provides a process of using the 5-alkyl-6-[[amino]methyl]pyrido[2,3-d]pyrimidine derivatives and new pyrido[2,3-d]pyrimidine, pyrido[3,2-d]pyrimidine and quinazoline derivatives of FIGS. 1–6 described herein for therapeutic purposes including employing these compounds as antitumor, antibiotic, antimalarial, antifungal and antiprotozoal agents and as synergistic agents with sulfonamides. Derivatives of the 5-alkyl-6-[[amino]methyl]pyrido[2,3-d]pyrimidine compounds and the pyrido[2,3-d]pyrimidine, pyrido[3,2-d]pyrimidine and quinazoline compounds and pharmaceutically acceptable salts of this invention substantially inhibit dihydrofolate reductase enzymes. This invention provides a process of using the 5-alkyl-6-[[amino]methyl]pyrido[2,3-d]pyrimidine derivatives, pyrido[2,3-d]pyrimidine, the pyrido[3,2-d]pyrimidine and quinazoline derivatives for therapeutic purposes as antiprotozoal and antifungal agents effective against secondary infections caused by *Pneumocystis carinii* and *Toxoplasmosis gondii* in immunocompromised patients such as for example patients with AIDS. The immunocompromised patient has a primary infection caused by a retrovirus including human immunodeficiency virus (HIV).

It is an object of this invention to provide 5-alkyl-6-[[amino]methyl]pyrido[2,3-d]pyrimidine compounds and pharmaceutically acceptable salts for substantially inhibiting dihydrofolate reductase enzymes.

It is an object of the present invention to provide 5-alkyl-6-[[amino]methyl]pyrido[2,3-d]pyrimidine compounds and pharmaceutically acceptable salts having antitumor, antibiotic, antimalarial, antifungal or antiprotozoal activity or synergistic activity with sulfonamides.

It is a further object of this invention to provide 5-alkyl-6-[[amino]methyl]pyrido[2,3-d]pyrimidine compounds and pharmaceutically acceptable salts having effective activity against secondary infections, such as for example infections caused by *Pneumocystis carinii* and *Toxoplasmosis gondii* that occur in immunocompromised patients, such as for example patients with AIDS.

It is an object of this invention to provide a method of preparing 5-alkyl-6-[[amino]methyl]pyrido[2,3-d]pyrimidine compounds and pharmaceutically acceptable salts thereof.

It is a further object of this invention to provide a method of using in a patient a therapeutically effective amount of 5-alkyl-6-[[amino]methyl]pyrido[2,3-d]pyrimidine compounds and pharmaceutically acceptable salts thereof.

It is a further object of this invention to provide a method of using in a patient a prophylactically effective amount of 5-alkyl-6-[[amino]methyl]pyrido[2,3-d]pyrimidine compounds and pharmaceutically acceptable salts thereof.

It is an object of this invention to provide derivatives of pyrido[2,3-d] and [3,2-d]pyrimidine and quinazoline compounds and pharmaceutically acceptable salts of FIGS. 2–6 for substantially inhibiting dihydrofolate reductase enzymes.

It is an object of the present invention to provide derivatives of pyrido[2,3-d] and [3,2-d]pyrimidine and quinazoline compounds and pharmaceutically acceptable salts of FIGS. 2–6 having antitumor, antibiotic, antimalarial, antifungal or antiprotozoal activity or synergistic activity with sulfonamides.

It is a further object of this invention to provide derivatives of pyrido[2,3-d] and [3,2-d]pyrimidine and quinazoline compounds and pharmaceutically acceptable salts of FIGS. 2–6 having effective activity against secondary infections, such as for example infections caused by Pneumocystis carinii and Toxoplasmosis gondii that occur in immunocompromised patients, such as for example patients with AIDS.

It is an object of this invention to provide a method of preparing derivatives of pyrido[3,2-d] and pyrido[2,3-d] pyrimidines and quinazoline compounds and pharmaceutically acceptable salts of FIGS. 2–6 thereof.

It is further object of this invention to provide a method of using in a patient a therapeutically effective amount of derivatives of pyrido[3,2-d]pyrimidine, pyrido[2,3-d] pyrimidine and quinazoline compounds and pharmaceutically acceptable salts of FIGS. 2–6 thereof.

It is a further object of this invention to provide a method of using in a patient a prophylactically effective amount of derivatives of pyrido[3,2-d] and pyrido[2,3-d]pyrimidines and quinazoline compounds and pharmaceutically acceptable salts of FIGS. 2–6 thereof.

These and other objects of the invention will be more fully understood from the drawing and the following description of the invention and the claims appended hereto.

DESCRIPTION OF THE PREFERRED EMBODIMENT

Figure 1:
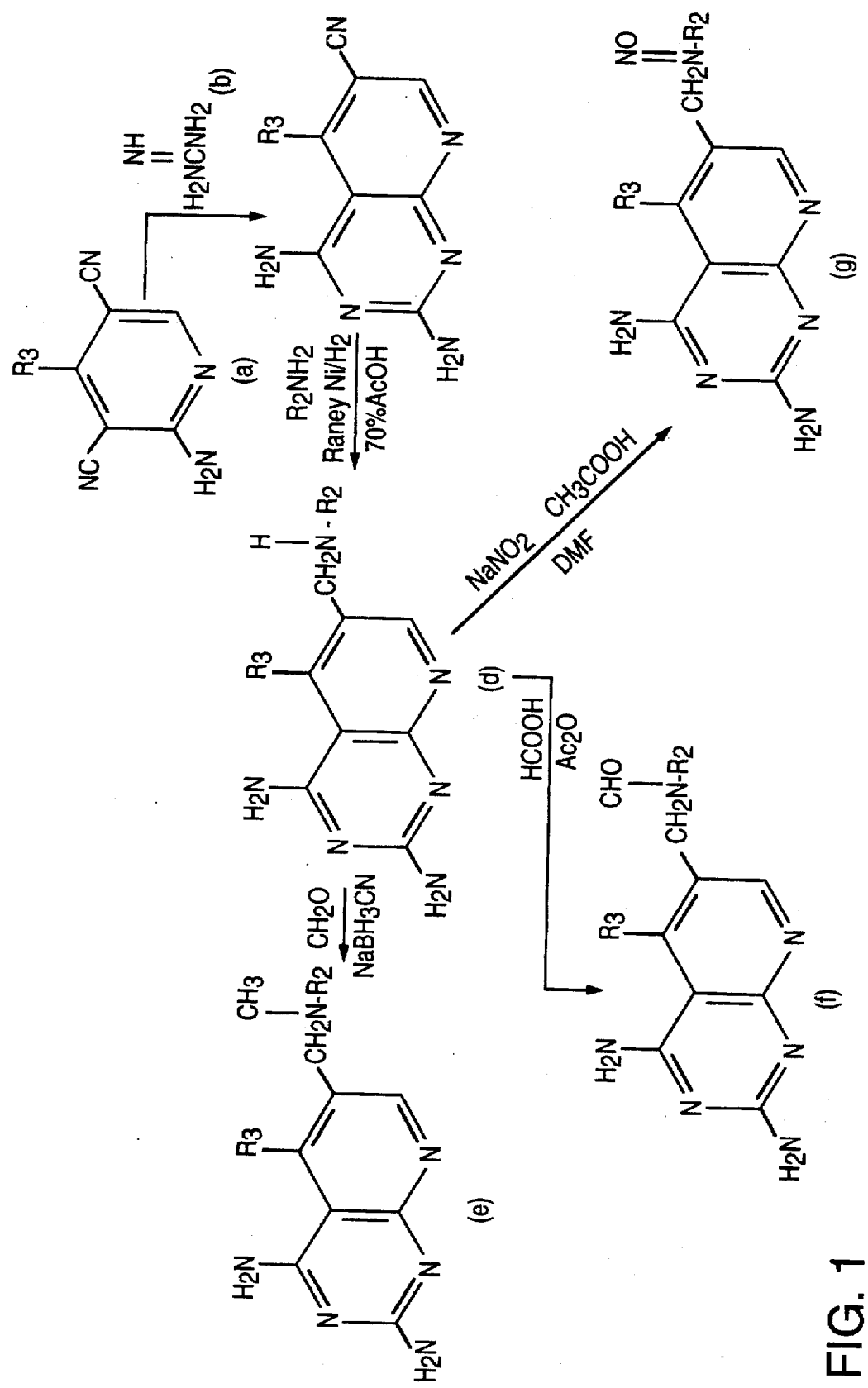
FIG. 1 shows a schematic diagram of the general chemical structure of the compounds and derivatives of this invention and the method of preparing these compounds and derivatives.

As used herein, the term "patients" means members of the animal kingdom including but not limited to human beings.

The 5-alkyl-6-[[amino]methyl]pyrido[2,3-d]pyrimidine derivatives and the pyrido[3,2-d] and pyrido [2,3-d] pyrimidines and quinazoline compounds and pharmaceutically acceptable salts and methods of preparing and using the compounds of this invention provide antitumor, antibiotic, antifungal, antimalarial and antiprotozoal agents, and synergistic agents with sulfonamides. The compounds of this invention provide for the therapeutic and prophylactic treatment of secondary infections caused by Pneumocystis carinii and Toxoplasmosis gondii in immunocompromised patients. The patients have a primary infection caused by a retrovirus including human immunodeficiency virus (HIV).

The 5-alkyl-6-[[amino]methyl]pyrido[2,3-d]pyrimidine compounds and pyrido[3,2-d] and pyrido[2,3-d]pyrimidines and quinazoline compounds and pharmaceutically acceptable salts of this invention inhibit the dihydrofolate reductase (DHFR) enzymes. The DHFR enzymes are needed for normal cell growth. It is known by those skilled in the art that 5,10-methylenetetrahydrofolate is essential for cell growth. It is also well known to those skilled in the art that dihydrofolate reductase reduces dihydrofolate to tetrahydrofolate. The derivatives of the present invention inhibit dihydrofolate reductase and consequently inhibit DNA synthesis. Inhibition of DNA synthesis results in cell death. The compounds and pharmaceutically acceptable salts of this invention have the general formula (1):

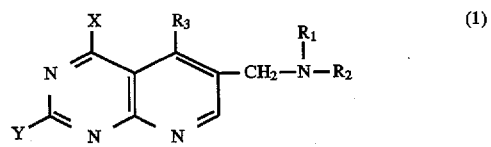

wherein X and Y are the same or different and are selected from the group consisting of OH and $NH_2$. $R_1$ is selected from the group consisting of hydrogen, a first lower alkyl group, a nitroso group and an aldehyde. $R_2$ is selected from the group consisting of a second lower alkyl group which is the same as or different than the first lower alkyl group, an aryl group, an alkylaryl group, a substituted aryl group and a substituted alkylaryl group. Each substituent of the substituted aryl group of the substituted alkylaryl group is the same or different and is selected from the group consisting of a third lower alkyl group which is the same as or different than the first lower alkyl group or the second lower alkyl group, an alkoxy group, a substituted alkoxyaryloxy group and a halogen; and wherein $R_3$ is a fourth lower alkyl group which is the same as or different than the first lower alkyl group, the second lower alkyl group or the third lower alkyl group.

The compounds and pharmaceutically acceptable salts of this invention also have the generic formula (2):

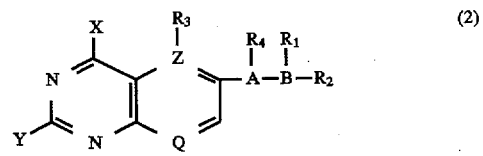

wherein X and Y are the same or different and are selected from the group consisting of OH and $NH_2$; Z is one of either N or C and Q is one of either N or C but when Z equals N, Q does not equal nitrogen A is selected from the group consisting of nitrogen, carbon and sulfur B equals carbon when A is selected from the group consisting of sulfur, carbon and nitrogen, B equals nitrogen when A equals carbon, and B equals sulfur when A equals carbon; $R_3$ is one of hydrogen or methyl except where Z is nitrogen where $R_3$ is nothing; $R_4$ is one of either a hydrogen or a first lower alkyl group except when A equals sulfur wherein $R_4$ is nothing; $R_1$ is selected from the group consisting of hydrogen, a nitroso group, an aldehyde, a second lower alkyl group which is the same or different than the first lower alkyl group except when B is equal to sulfur wherein $R_1$ is nothing; $R_2$ is selected from the group consisting of a third lower alkyl group which is the same or different than the first lower and second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group, and a substituted triaryl group. Each substituent of the substituted aryl group, diaryl group, triaryl group or the substituted alkyl group, alkyldiaryl group, alkyltriaryl group is the same or different and is selected from the group consisting of a fourth lower alkyl group which is the same or different than the first lower alkyl group, the second lower alkyl group, and the third lower alkyl group, and the third lower alkyl group, an alkoxy, a substituted alkoxyaryloxy group and a halogen.

The first species of the generic structure shown in (2) is the compounds and pharmaceutically acceptable salts having the formula (3)

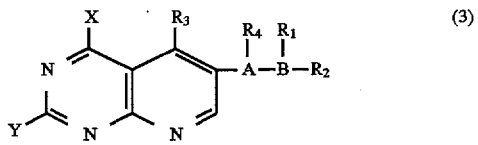

wherein X and Y may be the same or different and are selected from the group consisting of OH and $NH_2$; A is selected from the group consisting of nitrogen, carbon and sulfur and B equals carbon when A is selected from the group consisting of sulfur, carbon and nitrogen or B equals nitrogen when A equals carbon and B equals sulfur when A equals carbon. $R_3$ is one of either hydrogen or methyl; $R_4$ is one of either H or a first lower alkyl group except when A equals sulfur wherein $R_4$ is zero; $R_1$ is selected from the group consisting of hydrogen, a nitroso group, an aldehyde, a second lower alkyl group which is the same or different from the first lower alkyl group except when B is equal to sulfur wherein $R_1$ is equal to sulfur; $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group and a substituted triaryl group, and each substituent of the substituted aryl group, diaryl group and triaryl group or the substituted alkylaryl group, alkyldiaryl group and alkyltriaryl group is the same or different and is selected from the group consisting of a fourth lower alkyl group which is the same as or different from the first lower alkyl group, the second lower alkyl group and the third lower alkyl group, a substituted alkoxy group, aryloxy group and a halogen.

The compounds and pharmaceutically acceptable salts of the second species of the generic structure shown in (2) has the formula (4)

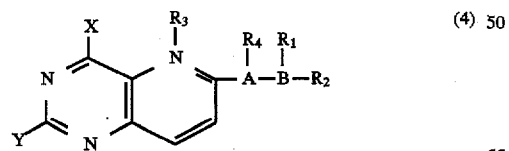

wherein X and Y may be the same or different and are selected from the group consisting of OH and $NH_2$; A is selected from the group consisting of nitrogen, carbon and sulfur; B equals carbon when A is selected from the group consisting of sulfur, carbon and nitrogen or B equals nitrogen when A equals carbon or B equals sulfur when A equals carbon wherein $R_3$ is zero; $R_4$ is one of either a hydrogen or a first lower alkyl group except where A equals sulfur wherein $R_4$ is zero; $R_1$ is selected from the group consisting of a hydrogen, a nitroso group, an aldehyde, a second lower alkyl group which is the same or different than the first lower alkyl group except when B is equal to sulfur where $R_1$ is equals to zero; $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, a substituted diaryl group and a substituted triaryl group and each substituent of the substituted aryl group, diaryl group, triaryl group or the substituted alkylaryl group, alkyldiaryl group, alkyltriaryl group is the same or different and is selected from the group consisting of a fourth lower alkyl group which is the same or different than the first lower alkyl group, the second lower alkyl group, the third lower alkyl group, a substituted alkoxy aryloxy group and a halogen.

The compounds and pharmaceutically acceptable salts of the third species of the generic structure shown in (2) has the formula (5)

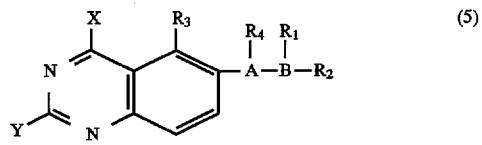

wherein X and Y are the same or different and are selected from the group consisting of OH and $NH_2$; A is selected from the group consisting of sulfur, carbon and nitrogen and B equals carbon when A is selected from the group consisting of sulfur, carbon and nitrogen or B equals nitrogen when A equals carbon and B equals sulfur when A equals carbon; $R_3$ is one of either a hydrogen or methyl; $R_4$ is one of either a hydrogen or a first lower alkyl group except where A equals sulfur wherein $R_4$ is zero; $R_1$ is selected from the group consisting of hydrogen, a nitroso group, an aldehyde, a second lower alkyl group which is the same or different than the first lower alkyl group except when B is equal to sulfur wherein $R_1$ is zero; $R_2$ is selected from the group consisting of a third lower alkyl group which is the same or different than the first lower alkyl. group and the second lower alkyl group, an aryl group, an alkylaryl group, a substituted aryl group, a substituted alkylaryl group, a diaryl group, a triaryl group, an alkyldiaryl group, an alk-yltriaryl group, a substituted diaryl group, a substituted triaryl group; each substituent of the substituted aryl group, diaryl group, triaryl group or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxy aryloxy group and a halogen.

The present invention also provides compounds and pharmaceutically acceptable salts which have the general formula (6)

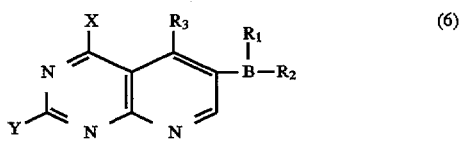

wherein X and Y may be the same or different and are selected from the group consisting of OH and $NH_2$; B is selected from the group consisting of nitrogen, carbon, sulfur and oxygen; $R_3$ is one of either hydrogen or methyl; $R_1$ is selected from the group consisting of hydrogen or a nitroso group, an aldehyde, a first lower alkyl group except when B is one of either sulfur or oxygen and $R_1$ is zero; $R_2$ is selected from the group consisting of a second lower alkyl group which is the same or different than the first lower alkyl group, an aryl group, an alkylaryl group, a substituted alkylaryl group, an alkyldiaryl group, an alkyltriaryl group, a substituted triaryl group and each substituent of the substituted aryl group, diaryl group, triaryl group or the substituted alkylaryl group, alkyldiaryl group and alkyltriaryl group is the same or different and is selected from the group consisting of a third lower alkyl group which is the same as or different from the first lower alkyl group, the second lower alkyl group, an alkoxy, a substituted alkoxyaryloxy group and a halogen.

For compound (1), the first, second, third and fourth lower alkyl groups are the same or different and are groups having one to about seven carbon atoms, such as for example methyl, ethyl, propyl, butyl, pentyl, hexyl or heptyl groups. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

Suitable aryl groups include for example phenyl and benzyl groups. Suitable substituted aryl groups include for example: mono-, di- and tri-substituted alkoxy phenyl groups; mono-, di- and tri-halogenated phenyl groups; mono-, di and tri-substituted alkyl phenyl groups; mono-, di- and tri-substituted alkoxy benzyl groups and mono-, di- and tri-substituted halogenated benzyl groups.

The term "alkylaryl" refers to groups having an alkyl moiety attached to an aryl ring such as a phenyl or benzyl ring. The alkyl moiety is preferably a lower alkyl chain having one to about seven carbon atoms. This alkyl moiety may also contain oxygen, nitrogen or sulfur atoms, such as for example methoxy groups. The aryl moiety of the alkylaryl group is unsubstituted, mono-substituted, di-substituted or tri-substituted. If substituted, each substituent may independently be selected from the group consisting of a lower alkyl group having one to about seven carbon atoms, an alkoxy group such as for example a methoxy group and a halogen, such as for example fluorine, chlorine or bromine.

In the generic compound (2) and species 3–5 and compound 6 and pharmaceutically acceptable salts of these compounds, the first lower alkyl group has one to about six carbon atoms selected from the group consisting of branched, unbranched and acyclic, the second lower alkyl group has one to about six carbon atoms selected from the group consisting of branched, unbranched and acyclic; wherein the alkylaryl group is selected from the group consisting of an alkylphenyl and alkylbenzyl group; wherein said alkyldiaryl group is selected from the group consisting of alkylnaphthyl, alkylbenzothiophene, alkylindene, alkylbenzofuran, alkylindole and alkylaminoquinoline; wherein the alkyltriaryl group is an alkylanthracyl group; wherein the substituted aryl, diaryl and triaryl group is selected from the group consisting of a mono-, di- and tri-substituted alkylphenyl and alkylbenzyl group, alkylnaphthyl, alkylbenzothiophene, alkylindole, alkylbenzofuran, alkylindene, alkylaminoquinoline, alkylanthracyl; wherein each substituted alkyldiaryl and alkyltriaryl group is selected from the group consisting of a mono-, di- and tri-substituted alkylnaphthyl, alkylbenzothiophene, alkylindole, alkylbenzofuran, alkylindene, alkylaminoquinoline and alkylanthraeyl group; and wherein each substituent is the same or different and is selected from the group consisting of methyl, ethyl, n-propyl, n-butyl, branched n-pentyl, branched pentyl, n-hexyl, branched hexyl, cyclopropyl, cyclobutyl, cyclopentyl, cyclohexyl, methoxy group, chlorine atom, bromine atom and fluorine atom.

Pharmaceutically acceptable salts for formulas 1–6 include, for example, acetate, formate, glucuronate, ethantale or sulfonate.

In formulas 1–6, when X and Y are the same or different and are selected from the group consisting of OH and $NH_2$ groups, the enol form of the compounds is represented. The enol form is equivalent to and includes the keto form of the compounds.

In a most preferred embodiment of FIG. 1 of this invention, compounds and pharmaceutically acceptable salts are provided having formula 1 and (a) wherein X and Y are each $NH_2$, $R_1$ is hydrogen, $R_2$ is 3,4,5-trimethoxyphenyl and $R_3$ is $CH_3$ (Compound I), or (b) wherein X and Y are each $NH_2$, $R_1$ is $CH_3$, $R_2$ is 3,4,5-trimethoxyphenyl and $R_3$ is $CH_3$ (Compound II), or (c) wherein X and Y are each $NH_2$, $R_1$ is CHO, $R_2$ is 3,4,5-trimethoxyphenyl and $R_3$ is $CH_3$ (Compound III). Compounds I, II and III and pharmaceutically acceptable salts are preferred in resisting secondary infections caused by *Pneumocystis carinii* and *Toxoplasmosis gondii* in immunocompromised patients.

In a most preferred embodiment of formula 3, compounds and pharmaceutically acceptable salts are provided having the given formula 3 and (a) wherein X and Y are each $NH_2$, $R_3$ is hydrogen, A is nitrogen, $R_4$ is $CH_3$, B is C, $R_1$ is H, and $R_2$ is 2',5'-dimethoxyphenyl or (b) wherein X and Y are each $NH_2$, $R_3$ is hydrogen, A is carbon, $R_4$ is hydrogen, B is nitrogen, $R_1$ is hydrogen, $R_2$ is 4'-methoxynaphthyl; or (c) wherein X and Y are both $NH_2$, $R_3$ is H, A is carbon, $R_4$ is H, B is sulfur, $R_1$ is zero, $R_2$ is 3',4',5'-trimethoxyphenyl; or (d) wherein X and Y are both $NH_2$, $R_3$ is hydrogen, A is carbon, $R_4$ is H, B is nitrogen, $R_1$ is hydrogen and $R_2$ is 3,4,5-trimethoxyphenyl. Compounds (a), (b), (c) and (d) and pharmaceutically acceptable salts are preferred in resisting secondary infections caused by *Pneumocystis carinii* and *Toxoplasmosis gondii* in immunecompromised patients.

In a most preferred embodiment of formula (4) compounds and pharmaceutically acceptable salts are provided having the general formula 4 and (a) wherein X and Y are each $NH_2$, A is carbon, $R_4$ is hydrogen, B is sulfur, $R_1$ is zero, and $R_2$ is 2',5'-dimethoxyphenyl; or (b) wherein X and Y are both $NH_2$, A is nitrogen, $R_4$ is $CH_3$, B is carbon, $R_1$ is hydrogen and $R_2$ is 2',5'-dimethoxyphenyl; (c) wherein X and Y are each $NH_2$, A is carbon, $R_4$ is hydrogen, B is carbon, $R_1$ is hydrogen and $R_2$ is 3',4',5'-trimethoxyphenyl; and (d) wherein X and Y are each $NH_2$, A is nitrogen, $R_4$ is hydrogen, B is carbon, $R_1$ is hydrogen and $R_2$ is 1'-naphthyl. Compounds a, b, c and d and pharmaceutically acceptable salts are preferred in resisting secondary infections caused by *Pneumocystis carinii* and *Toxoplasmosis gondii* in immunocompromised patients.

In a most preferred embodiment of formula 5 compounds and pharmaceutically acceptable salts are provided having the general formula 5 and (a) wherein X and Y are each $NH_2$, A is sulfur, $R_4$ is zero, B is carbon, $R_1$ is hydrogen and $R_2$ is 3,4,5-trimethoxyphenyl, or (b) wherein X and Y are each $NH_2$, A is carbon, $R_4$ is hydrogen, B is nitrogen, $R_1$ is methyl and $R_2$ is 2',5'-dimethoxyphenyl or (c) wherein X and Y are each $NH_2$, A is carbon, $R_4$ is hydrogen, B is carbon, $R_1$ is hydrogen and $R_2$ is naphthyl.

In a most preferred embodiment of formula (6) compounds and pharmaceutically acceptable salts are provided having the general formula (6) and (a) wherein X and Y are each $NH_2$, $R_3$ is hydrogen, B is sulfur, $R_1$ is zero and $R_2$ is 2',5'-dimethoxyphenyl, and (b) wherein X and Y are each NH$_2$, R$_3$ and hydrogen; B is carbon; R$_1$ is hydrogen and R$_2$ is 2',5'-dimethoxyphenyl.

In a preferred embodiment is this invention, compounds and pharmaceutically acceptable salts are provided having the general formula 1 and formulas 2–6 wherein X and Y are each NH$_2$, R$_1$ is selected from the group consisting of H, CH$_3$ and CHO, CH$_3$CHO, and zero and R$_2$ is selected from the group consisting of 2,5-dimethoxyphenyl, 2,3,4-trimethoxyphenyl, 2,4,6-trimethoxyphenyl, naphthyl, 4-methoxynaphthyl, anthracyl and methoxy anthracyl, florene, benzothiophene, indene, benzofuran, indole, aminoquinoline, 2,3-diehlorophenyl, 2,4-dichlorophenyl, 2,5-dichlorophenyl, 2,6-dichlorophenyl, 3,4-dichlorophenyl and 3,5-dichlorophenyl. R$_3$ is CH$_3$ or hydrogen, R$_4$ in formulas 3–5 are a hydrogen, methyl, ethyl, propyl and butyl group, cyclopropyl, cyclobutyl and cyclohexyl and zero, B in formula 6 is selected from the group consisting of nitrogen, carbon, sulfur and oxygen, B in formulas 3–5 is selected from the group consisting of carbon, nitrogen, sulfur, A in formulas 3–5 is selected from the group consisting of nitrogen, carbon and sulfur.

In another embodiment of this invention, compounds and pharmaceutically acceptable salts are provided having the given formula 1 and formulas 3–6 wherein X and Y are each NH$_2$. R$_1$ is selected from the group consisting of H, CH$_3$, NO and CHO, CH$_3$CHO, zero. R$_2$ is selected from the group consisting of 2-methoxyphenyl, 3-methoxyphenyl, 4-methoxyphenyl, 2,4-dimethoxyphenyl, 3,4-dimethoxyphenyl, 3-5-dimethoxyphenyl, 2-chlorophenyl, 3-chlorophenyl, 4-chlorophenyl, 2,3,4-trichlorophenyl, 2,4,5-trichlorophenyl, 2,4,6-trichlorophenyl, 3,4,5 - trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5 -dibromophenyl, 2,4,6-tribromophenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,4,5-trifluorophenyl, 2,4,6-trifluorophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,5-trimethylphenyl, and 2,4,6-trimethylphenyl. R$_3$ is CH$_3$ or hydrogen, and in formulas 3–5. R$_4$ is selected from the group consisting of hydrogen, methyl, ethyl, propyl, and butyl group, cyclopropyl, cyclobutyl, cyclohexyl and zero. B in formula 6 is selected from the group consisting of nitrogen, carbon, sulfur and oxygen; B in formulas 3–5 is selected from the group consisting of carbon, nitrogen and sulfur; A in formulas 3–5 is selected from the group consisting of nitrogen, carbon and sulfur.

In a less preferred embodiment of this invention, compounds and pharmaceutically acceptable salts are provided having the given formula 1 wherein X and Y are each NH$_2$. R$_1$ is selected from the group consisting of H, CH$_3$, NO and CHO, CH$_3$CHO, zero. R$_2$ is selected from the group consisting of methyl, ethyl, n-propyl, n-butyl, cyclopropyl, cyclobutyl, cyclopentyl, cyclohexyl, 2-methoxybenzyl, 3,4-dimethoxybenzyl, 2,3-dimethoxybenzyl, 3,4-dimethoxybenzyl, 2,3,4-trimethoxybenzyl, 3,4,5-trimethoxybenzyl, 2-chlorobenzyl, 3,4-dichlorobenzyl, 2,3-dichlorobenzyl, 2,4-dichlorobenzyl, 2,5-dichlorobenzyl, 2,6-dichlorobenzyl, 2,6-dichlorobenzyl, 3,4-dichlorobenzyl, 3,5-dichlorobenzyl, 2-bromobenzyl, 3,4-dibromobenzyl, 2-fluorobenzyl, 3,4-difluorobenzyl, 2,4-difluorobenzyl, 2,5-difluorobenzyl, 2,6-difluorobenzyl and 3,4-difluorobenzyl. R$_3$ is CH$_3$ and hydrogen, and in formulas 3–5 R$_4$ is selected from the group consisting of a hydrogen, methyl, ethyl, propyl, butyl group, cyclopropyl, cyclobutyl, cyclohexyl; B in formula 6 is selected from the group consisting of nitrogen, carbon, sulfur and oxygen; B in formulas 3–5 is selected from the group consisting of nitrogen, carbon and sulfur; A in formulas 3–5 is selected from the group consisting of nitrogen, carbon and sulfur.

EXAMPLE I

Compounds I, II and III were evaluated as inhibitors of dihydrofolate reductase (DHFR) from *Pneumocystis carinii* (Pc) and *Toxoplasmosis gondii* (Tx) and rat liver (RL). Compounds I, II and II were compared in this respect with trimetrexate. Trimetrexate is available from Warner-Lambert/Parke Davis Pharmaceutical Research, Ann Arbor, Mich. Trimetrexate is approved by the United States Food and Drug Administration as an approved new drug for the treatment of *Pneumocystis carinii* infections in patients with AIDS.

The evaluations of Compounds I, II and III consisted of determining the IC$_{50}$ values and selectivity ratios of each compound. The IC$_{50}$ value is the concentration of a compound required to inhibit the dihydrofolate reductase activity by 50 percent (%). It will be understood by those skilled in the are that the lower the IC$_{50}$ value the more potent the compound. The selectivity ratio is a measure of the selectivity of a compound for Pc DHFR or Tx DHFR and is expressed as the IC$_{50}$ value of the DHFR from rate liver (RL) divided by the IC$_{50}$ value of the DHFR of *Pneumocystis carinii* (Pc) and *Toxoplasmosis gondii* (Tx). For example, the selectivity ratio of a compound is calculated by the following formula (7):

$$\frac{IC_{50}\ RL\ DHFR}{IC_{50}\ (Pc\ DHFR\ or\ Tx\ DHFR)}$$

It will be understood by those skilled in the art that the higher the number of the selectivity ratio, the less toxic the compound is to mammalian dihydrofolate reductase, and thus, less toxic.

Table I sets forth the IC$_{50}$ values for Pc DHFR, RL DHFR and Tx DHFR and the corresponding selectivity ratios for Compounds I, II and III and trimetrexate.

TABLE I

| DHFR | Pc DHFR[1] | RL DHFR[1] | Selectivity Ratio: RL DHFR/Pc DHFR | Tx DHFR[1] | Selectivity Ratio RL DHFR/Tx |
|---|---|---|---|---|---|
| Compound I | 86.0 | 2.1 | 0.02 | 7.4 | 0.28 |
| Compound II | 13.2 | 7.6 | 0.58 | 0.85 | 8.94 |
| Compound III | 550.0 | 110.0 | 0.20 | 13.0 | 8.46 |
| Trimetrexate | 42.0 | 3.0 | 0.072 | 10.0 | 0.29 |

[1]Values of $IC_{50}$ in nanomoles (nM). One nanomole = $1 \times 10^{-9}$ mole.

From Table I, it will be appreciated that Compounds I, II and III are each potent inhibitors of all the DHFRs tested.

Table I shows that Compound I has an $IC_{50}$ value of 86 nM (nanomoles) and is generally about two times less active than trimetrexate on *Pneumocystis carinii* DHFR and has about the same activity as trimetrexate on *Toxoplasmosis gondii* DHFR. The selectivity ratio of 0.02 of Compound I for Pc DHFR is less than trimetrexate but the selectivity ratio of 0.28 of Compound I for Tx DHFR is generally equal to trimetrexate.

Compound II is the most active and the most selective of the four compounds tested. Compound II with an $IC_{50}$ value of 13.2 nM is more than three times more active than trimetrexate on Pc DHFR and has a selectivity ratio of 0.58 which is about eight times less toxic than trimetrexate. In Tx DHFR, Compound II with an $IC_{50}$ value of 0.85 nM is about twelve times more active than trimetrexate and has a selectivity ratio of 8.94 which is about thirty-one times less toxic than trimetrexate. Compound II is the most potent analogue known at the present time with regard to Tx DHFR inhibition.

Compound III with an $IC_{50}$ value of 550 nM is about thirteen times less active than trimetrexate in Pc DHFR and has a selectivity ratio of 0.20 which is about three times less toxic than trimetrexate. However, Compound III with an $IC_{50}$ value of 13 nM has about the same activity as trimetrexate in Tx DHFR but has a selectivity ratio of 8.46 which is about twenty-nine times less toxic than trimetrexate.

These results indicate that the compounds of this invention are significantly active in Pc DHFR and in Tx DHFR and that Compound II is the most preferred compound of this invention for the treatment of infections caused by *Pneumocystis carinii* and *Toxoplasmosis gondii*. With regard to *Pneumocystis carinii*, Compound II with its high potency and high selectivity may be used clinically with a lesser amount of leucovorin or may be used clinically without the necessity of leucovorin, and thus greatly reduce the cost of administering this compound to a patient.

$IC_{50}$ values of human DHFR (hDHFR) and derived selectivity ratios against human DHFR have been determined and they are meaningful for the following compounds in Table II, the values from formula (8) are dramatic:

$$\frac{IC_{50} \, hDHFR}{IC_{50} \, (Pc \, DHFR \, or \, Tx \, DHFR)} \quad (8)$$

Figure 2:
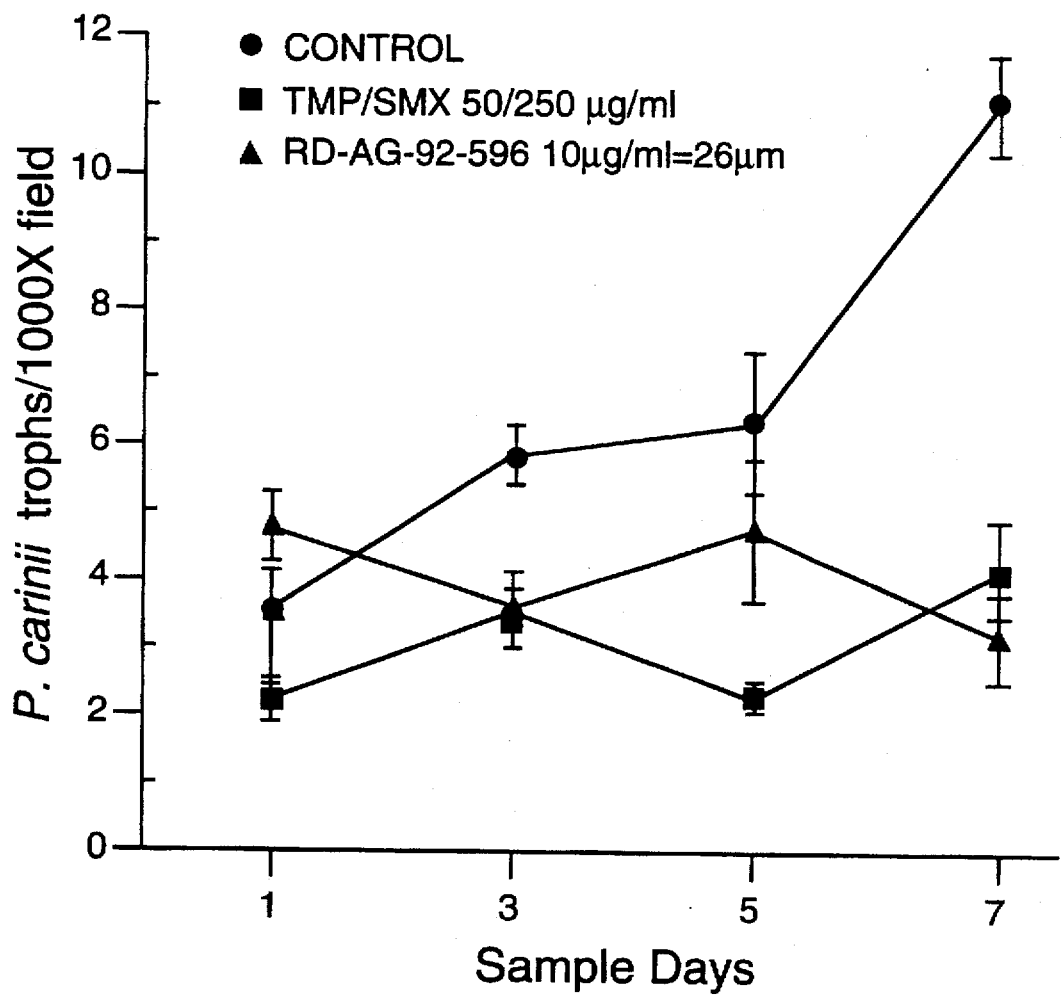
FIG. 2 shows the inhibition of Pneumocystis carinii cells by 2,4-diamino-6-[3',4',5'-trimethyoxyanilinomethyl]pyrido [2,3-d]pyrimidine.

Compound 1 shows excellent selectivity of 17.8 against pcDHFR and an astounding selectivity of 714 against tgDHFR. Compound 2 shows a selectivity of 9.5 against pcDHFR and a very high selectivity of 161.5 against tgDHFR. Compound 3, the N9-CH$_3$ analog of 1, shows that N9-methylation increases potency in pcDHFR and hDHFR by about three orders of magnitude and about an order in tgDHFR; however, the selectivity against both pcDHFR and tgDHFR are reduced compared to 1. Thus, for the reversed analogs (N9-C10) with 3,4,5-triOCH$_3$Ph substitution N9-methylation is conducive to potency but detrimental to selectivity. It is clear from Table II that in compounds 2 and 3 a change in the nature of the 9–10 bridge provides for significantly different activities and selectivities. Based on a comparison with TMQ (which has been recently approved for treatment of *Pneumocystis carinii* infections, only with leucovodn rescue, due to toxicity) all of the 5-desmethyl analogs 1–4 and 6 are significantly more selective in pcDHFR and tgDHFR. Compound 1 was fourteen times more selective in pcDHFR and one hundred and thirty-four times more selective against tgDHFR than TMQ. However, activity against pcDI-IFR of compound 1 is significantly lower, but the activity of 1 compared to TMQ in tgDHFR is only about an order of magnitude less with a 134-fold increase in selectivity. The other analogs 2 and 3 have similar potencies (except 2 in pcDHFR) with much better selectivites than TMQ. The activities of compounds 1 and 3 in other DHFRs and their selectivities are included to further substantiate that the 5-desmethylpyrido[2,3-d]pyrimidines indeed possess significant selectivity against a variety of different DHFRs compared with hDHFR. Preliminary studies of 2 for the inhibition of *Pneumocystis carinii* cells in culture is shown in FIG. 2. At 10 µg/mL compounds 2 was as effective as TMP/SMX 50/250 µg/mL. An indication of the ability of compound 3 to penetrate cells in culture is provided by the data obtained from the preclinical screening program of the National Cancer Institute. The GI$_{50}$ for this reversed analog was $10^{-7}$ M in tumor systems which was in good agreement with its $IC_{50}$ of $2.6 \times 10^{-7}$ M against hDHFR. Compound 1 was also tested but had GI$_{50}$ values $<1.0 \times 10^{-4}$. However, tumor cell inhibitory results of compound 1 attests to its poor hDHFR inhibitory potency, and hence its selectivity. In addition, Table II shows that compounds 1 and 4 are also highly selective towards bacteria DHFRs such as *L. casei*, *E. coli* and *S. faecium*.

TABLE II

DHFR INHIBITION IC$_{50}$M AND SELECTIVITY RATIOS

|  | X | hDHFR | pcDHFR | Selectivity hDHFR pcDHFR | tgDHFR | Selectivity hDHFR tgDHFR | lcDHFR | Selectivity hDHFR lcDHFR | ecDHFR | Selectivity hDHFR ecDHFR | sfDHFR | Selectivity hDHFR sfDHFR |
|---|---|---|---|---|---|---|---|---|---|---|---|---|
| 1 | —NCH$_2$—H | $2.5 \times 10^{-4}$ | $1.4 \times 10^{-5}$ | 17.8 | $3.5 \times 10^{-7}$ | 714 | $2.5 \times 10^{-6}$ | 100 | $1.0 \times 10^{-7}$ | 2500 | $5.1 \times 10^{-8}$ | 4902 |
| 2 | —CH$_2$N—CH$_3$ | $2.1 \times 10^{-6}$ | $2.19 \times 10^{-7}$ | 9.5 | $1.3 \times 10^{-8}$ | 161.5 | ND | ND | ND | ND | ND | ND |
| 3 | —NCH$_2$—CH$_3$ | $2.6 \times 10^{-7}$ | $6.1 \times 10^{-8}$ | 4.3 | $1.4 \times 10^{-8}$ | 18.0 | $2.6 \times 10^{-8}$ | 10 | $5.0 \times 10^{-9}$ | 52 | $2.7 \times 10^{-9}$ | 96 |
| 4 | —NCH$_2$—H | $2.7 \times 10^{-5}$ | $5.5 \times 10^{-6}$ | 4.9 | $4.8 \times 10^{-7}$ | 56.0 | $2.7 \times 10^{-6}$ | 10 | $1.3 \times 10^{-7}$ | 207 | $1.5 \times 10^{-8}$ | 1800 |
| 5 | 2',4',5'-triOCH$_3$ —NCH$_2$-2',5'-diOCH$_3$ | $1.3 \times 10^{-5}$ | $3.8 \times 10^{-6}$ | 3.4 | $3.1 \times 10^{-7}$ | 41 | $5.1 \times 10^{-6}$ | 2.5 | $1.3 \times 10^{-7}$ | 100 | $1.5 \times 10^{-8}$ | 866 |
|  | Trimetrexate (TMQ) | $5.3 \times 10^{-8}$ | $4.2 \times 10^{-8}$ | 1.26 | $1.0 \times 10^{-8}$ | 5.3 | $3.5 \times 10^{-8}$ | 1.51 | $1.7 \times 10^{-9}$ | 31 | $1.8 \times 10^{-9}$ | 29 |
| 6 | —N—CH$_2$—CH$_3$ 2',5'-diOCH$_3$ | $8.5 \times 10^{-6}$ | $8.4 \times 10^{-8}$ | 101.9 | $6.3 \times 10^{-9}$ | 1349 | $5.7 \times 10^{-6}$ | 1.49 | $1.4 \times 10^{-7}$ | 60.7 | $2.8 \times 10^{-8}$ | 303.57 | hDHFR = human DHFR (recombinant); pcDHFR = P. carinii DHFR; tgDHFR = T. gondii DHFR; lcDHFR = L. casei DHFR; ecDHFR = E. coli DHFR; sfDHFR = S. faecium DHFR Compound 6 in Table II is the most selective compound in the table against pcDHFR with a ratio of 101.9. In addition, it is almost as potent against pcDHFR as clinically used TMQ and is 80 times more selective than TMQ. Against tgDHFR, compound 6 is about 10 times more potent than TMQ and 254 times more selective.

Table 3 (a) and (b) shows that a two-ring system for R$_2$ is much better than one ring for cell penetration. For example, the fn:st compound is much less potent than the last compound but the cell culture data for the first compound is 100 times better than the last compound in Table 3, showing that multiple rings for R$_2$ in some instances are better for cell penetration than single rings.

A further embodiment of this invention provides methods for preparing the hereinbefore described compounds and pharmaceutically acceptable salts thereof. The method of preparing the compounds and pharmaceutically acceptable salts of this invention is set forth generally in FIG. 1 and includes condensing 2-amino-3,5-dicarbonitrile-4-R$_3$-pyridine (represented by the letter "a" in FIG. 1) wherein R$_3$ is a lower alkyl group having one to about seven carbon atoms as described herein, such as for example, a methyl group, with guanidine (FIG. 1b) in refluxing ethyl alcohol to produce 2,4-diaminopyrido[2,3-d]pyrimidine-5-R$_3$-6-carbonitrile (FIG. 1c), subjecting 2,4-diaminopyrido[2,3-d]pyrimidine-5-R$_3$-6-carbonitrile (FIG. 1c) to reductive condensation with an alkyl amine, a substituted aniline or benzylamine derivative containing the R$_2$ group as described herein, such as for example, 3,4,5-trimethoxyaniline, and Raney nickel in aqueous acetic acid solution, and preferably about 70% acetic acid solution, to form 2,4-diamino-5-R$_3$-6-[[(R$_2$)amino]methyl]pyrido[2,3-d]pyrimidine (FIG. 1d). The starting material 2-amino-3,5-dicarbonitrile-4-R$_3$-pyridine (FIG. 1a) may be synthesized by those skilled in the art by modifying the method of Piper, et al., J. Med. Chem., Vol. 29, p. 1080 (1986).

These methods further include adding product "d" to about 37% formaldehyde in acetonitrile at about 25° Centigrade (C), adding sodium cyanoborohydride, glacial acetic acid and methanol, and refrigerating the reaction mixture overnight to form 2,4-diamino-5-R$_3$-6[[(R$_2$)methylamino]methyl]pyrido[2,3-d]pyrimidine (FIG. 1e).

A method to prepare 2,4-diamino-5-R$_3$-6[[(R$_2$)formylamino]methyl]pyrido[2,3-d]pyrimidine (FIG. 1f) includes reacting product "d" in about 98% formic acid as a solvent and acetic anhydride as a catalyst, removing the solvent under reduced pressure, diluting the reaction product with methanol and refrigerating the diluted reaction product overnight.

A method to prepare 2,4-diamino-5-R$_3$-6[[(R$_2$)nitrosoamino]methyl]pyrido[2,3-d]pyrimidine (FIG. 1g) includes reacting a chilled solution of product "d" in aqueous acetic acid and dimethyl formamide (DMF) and then adding NaNO$_2$ (sodium nitrate) in water. This mixture is stirred at about 0° C. to 5° C. for about two hours and then poured into dilute-sodium hydroxide.

It will be appreciated by those skilled in the art that by following the hereinbefore described methods of preparing products d, e, f and g of this invention that the derivatives of products d, e, f and g can be similarly prepared using the appropriate alkylamine, substituted aniline or benzylamine derivative containing the R$_2$ group as described herein.

Further, a method for preparing 4-amino-4-oxo derivatives of products d, e, f or g of this invention includes subjecting products d, e, f or g, respectively, to hydrolysis with 6N (six-normal solution) HCl for about six hours at room temperature.

Another embodiment of this invention is a method for preparing 2,4-dioxo derivatives of products d, e, f or g that includes subjecting product d, e, f or g, respectively, to hydrolysis with 6N HCl under mild reflux conditions for about two hours.

In order to further disclose a preferred method of preparing products d, e, f or g and derivatives thereof, the following examples are provided. Examples II, III and IV disclose methods of preparing Compound I, II and III, respectively.

EXAMPLE II

The following is an example of a method of making 6-(thiophenylmethyl)-2,4-diaminopyrido[2,3-d]pyrimidine (5) and 6-(thionapthylmethyl)-2,4-diaminopyrido[2,3-d]pyrimidine (6) of formula 3.

and stirred in anhydrous MeOH under $N_2$ overnight. $NaBH_4$ (0.17 g) was added in approximately four equal portions at intervals of 15 minutes (0.68 g total). The mixture was stirred for 5 additional hours. Insoluble material was filtered and the flitrate was treated with $H_2O$ (200 mL). The flitrate was the concentrated under reduced pressure at a temperature of 35° C. until a yellow precipitate began to form. The mixture was then refrigerated overnight, filtered and rinsed with $H_2O$, EtOH and $Et_2O$ to yield a yellow solid, 1.50 g. TLC (4:1:0.1 $CHCL_3$:MeOH:$NH_4OH$) showed a product spot at $R_f$=0.41 and a slight spot corresponding to the starting material. Separation was carried out by chromatography with silica gel.

6-(Bromomethyl)-2,4odiaminopyrido[2,3-d]pyrimidine (4). Crude alcohol (3) (0.24 g) was dried with $P_2O_5$ at 110° C. under vacuum overnight and then added to anhydrous

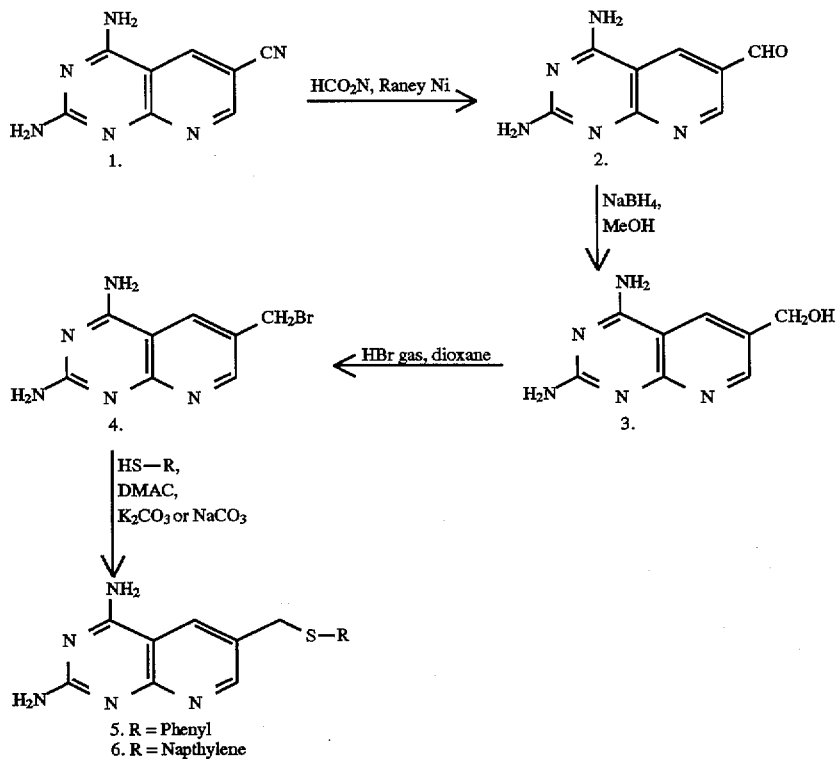

5. R = Phenyl
6. R = Napthylene 2,4-diaminopyrido[2,3-d]pyrimidine-6-carboxyaldehyde (2). The nitrile (1) (2.0 g, 10.8 mmol) was dissolved in warm $HCO_2H$ (60 mL, 88%) under $N_2$. Raney Ni (10 g damp) was added. The mixture was refluxed for 2 hours and filtered through Celite. The flitrate was concentrated under reduced pressure and a temperature of 50° C. with the aid of EtOH. The resulting viscous orange residue was then dissolved in boiling $H_2O$ (150 mL). The boiling solution was treated with Norit and filtered through Celite while hot. The filtrate was neutralized to pH 7 with 1N NaOH to give a yellow precipitate. The suspension was refrigerated overnight, filtered and washed with $H_2O$, EtOH and $Et_2O$ to give a yellow solid (1.75 g). Examination by TLC (4:1:0.1 $CHCl_3$:MeOH:$NH_4OH$) showed a dominant UV-absorbing spot at $R_f$=0.38 and contamination spots at $R_f$=0.19 and at baseline. The spot at $R_f$=0.19 was after chromatographic separation determined to correspond to the $R_f$ value of compound (3).

2,4-diaminopyrido[2,3-d]pyrimidine-6-methanol (3). Crude aldehyde (2) (5.0 g, 26.5 mmol) was pulverized, dried dioxane (10 mL). The mixture was stirred in an ice bath while dry HBr gas was bubbled through for 15 minutes, after which the flask was quickly stoppered. The mixture continued to stir and the alcohol dissolved after approximately ½ hour. The solution stirred for 24 hours and was then added dropwise to stirred $Et_2O$ under $N_2$ to give a yellow suspension. The suspension was refrigerated overnight, filtered and immediately dried with $P_2O_5$ under vacuum at 50° C. Yield: 45 mg.

6-(Thiophenylmethyl-2,4-diaminopyrido[2,3-d] pyrimidine (5). Phenylthiol (0.12 mL, 1.2 mmol) was dissolved in DMAC (10 mL) and added dropwise to compound (4) (0.25 g., 1.0 mmol). $K_2CO_3$ (~1 g) was added until the pH reached approximately 8. After 1 hour, compound (4) was not detectable by TLC (3:1:0.1 $CHCl_3$:MeOH:$NH_4OH$). The product spot appeared at $R_f$=0.33 with contamination spots at $R_f$=0.51 and at baseline. The solid was filtered and rinsed with $H_2O$, EtOH and $Et_2O$. Yield: 8%, 22 mg.

6-(Thionaphthylmethyl)-2,4-diaminopyddo[2,3-d]pyrimidine (6). Napthylenethiol (0.07 g, 0.45 mmol) was dissolved in DMAC (15 mL) and added dropwise to compound (4) (0.10 g, 0.4 mmol). $Na_2CO_3$ (0.3 g) was added and the color of the reaction mixture changed from yellow to green. The reaction was monitored by TLC (4:1:0.1 $CHCl_3$:MeOH:$NH_4OH$). The product spot occurred at $R_f$=0.5. After 3 hours, starting material was still present. Also, the yellow color returned. Allowed reaction to run overnight. The pH was then checked and found to be slightly acidic. Added solution dropwise to 1N $Na_2CO_3$ (100 mL). Stirred suspension for 15 minutes and refrigerated for 4 hours. Filtered solid and rinsed with $H_2O$, EtOH and $Et_2O$. Yield 19%, 25 mg.

EXAMPLE III

The following are various methods for making various 2,4-diamino-6-substituted-benzylamino pyrido[2,3-d]pyrimidines of formula 3.

The synthesis of the desired compounds was achieved via the reductive amination of 2,4-diamino-6 amino pyrido[2,3-d]pyrimidine 2, with the appropriately substituted aldehyde. A general scheme for the synthesis of these compounds is outlined below:

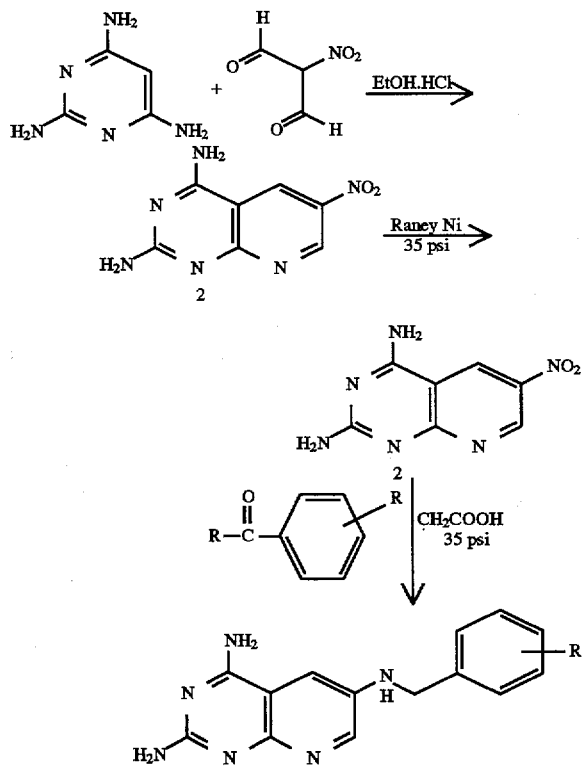

2,4-diamino-6-nitropyrido[2,3-d]pyrimidine, 1.

2,4,6-triamino pyrimidine (1 equiv.) was suspended in refluxing absolute ethanol (~50 ml) with stirring under an atmosphere of nitrogen. Concentrated HCl was added dropwise to effect solution and as soon as solution occurred, nitromalonaldehyde (1.2 equiv.) was added all at once. Within 10 minutes, a thick reddish voluminous precipitate started forming. TLC analysis indicated the presence of a yellow spot corresponding to that of the desired product along with staring materials. The reaction mixture was stirred at reflux for 3.5 hours, immediately diluted with 30 ml of water, cooled and neutralized with concentrated $NH_4OH$. The precipitate was collected on a funnel and was washed repeatedly with water to remove unreacted triamino pyrimidine to yield pure 2,4-diamino-6-nitropyrido[2,3-d]pyrimidine. Yield 85 %.

General procedure for the synthesis of 2,4-diamino-6-substituted-benzylamino pyrido[2,3-d]pyrimidines:

The 6-nitro compound (1 equiv.) was dissolved in N,N-dimethylformamide with heating. To this warm solution was added Raney Nickel (4–5 equiv. by weight) and the mixture was shaken in a Parry hydrogenator at 35 psi for 3.5 hours. At the end of this period, the appropriately substituted benzaldehyde (1 equiv.) or benzoketone (like acetophenone R=$CH_3$) was added and the mixture was hydrogenated for a further 3 hours. TLC analysis indicated the presence of a major uv absorbing spot corresponding to the product along with some unreacted 6-amino compound. The reaction mixture was filtered through Celite, ~1 g silica gel added to the filtrate and the fitrate evaporated to dryness. The resulting dry plug was chromatographed on a column using $CHCl_3$:MeOH(5:1) and fractions containing the pure product were pooled and evaporate to yield the pure compound in 30–40% yield.

2,4-diamino-6-[3',4',5'-trimethoxybenzylamino]pyrido[2,3-d]pyrimidine.

Yield=35%.

2,4-diamino-6-[2',5'-dimethoxy benzylamino]pyrido[2,3-d]pyrimidine.

Yield=32%.

2,4-diamino-6-[2',4',5'-trimethoxy benzylamino]pyrido[2,3-d]pyrimidine.

Yield=31%

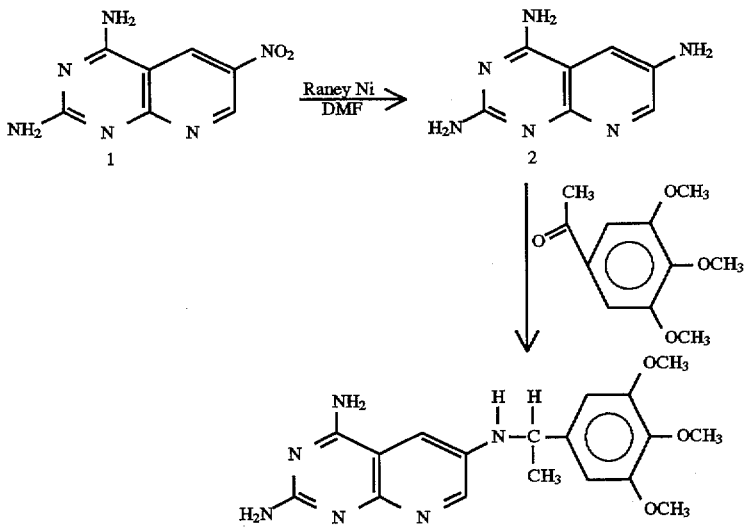

2,4-diamino-6-nitro pyrido[2,3-d] (0.3 g, 0.0014 mols) was dissolved in N,N-dimethylformamide (~100 ml) with warming. To this solution was added Raney Nickel (damp, 1 g) and the mixture hydrogenated at 35 psi for 4 hours. TLC analysis in $CHCl_3$:MeOH(5:1) indicated absence of all starting material ($R_f$=0.5) and the presence of an intensely fluorescent spot at $R_f$=0.3. The reaction mixture was filtered through Celite and the solvent evaporated using a vacuum pump (bath temp 75°). The residue was then triturated with ether, filtered and dried to yield crude 2. This solid was then suspended in methanol and 3,4,5-trimethoxyacetophenone (0.294 g, 0.0014 moles) was added and the reaction mixture stirred rigorously. $NaCNBH_3$ (0.264 g, 0.0042 moles) was added followed immediately by the dropwise addition of 1N HCl to affect solution. The reaction mixture was stirred at room temperature for 48 hours. At the end of this time, a small amount of water (~5 ml) was added to the reaction mixture and the solvents were evaporated completely. The residue was dissolved in methanol and 0.5 g of silica gel was added to the solution and the methanol stripped off to yield a dry plug. This was subjected to gradient L-column chromatography using $CHCl_3$:MeOH(100:1→80:20) as the eluant. Fractions 48–59 yielded a pure compound with $R_f$=0.59. The solvent was evaporated and the residue stirred in ether and filtered to yield a light yellow powder. Yield 78 mgs, 15%.

EXAMPLE IV

The following is a method of making 2,4-diamino-6-(anilinomethyl)pyrido[2,3-d]pyrimidines of formula 3.

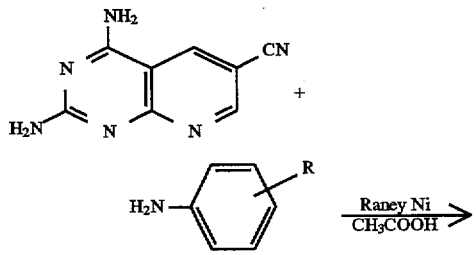

-continued

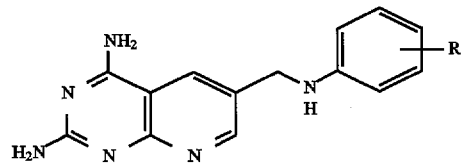

The 2,4-diamino-pyrido[2,3-d]pyrimidine-6-carbonitrile (1 equiv.) (achieved via literature procedures) was dissolved in 80% acetic acid. To this solution was added Raney Nickel (5 equiv.) followed immediately by the appropriately substituted aniline (1.5 equiv). The mixture was hydrogenated under atmospheric pressure and at room temperature for 6 hours. TLC analysis at the end of this period indicated the presence of a spot corresponding to the desired product. The reaction mixture was filtered through Celite and the flitrate was evaporated to dryness to yield a reddish residue. This residue was dissolved in warm absolute ethanol and then neutralized in the cold with 1N $Na_2CO_3$ dropwise with stirring to deposit the crude product. This solid was collected by filtration and was washed repeatedly with acetone, dissolved in a large volume of methanol, silica gel added and the methanol stripped off to yield a dry plug. Column chromatography using $CHCl_3$:MeOH(5:1) as the eluant yielded pure target compounds.

EXAMPLE V

The following is a method of making 2,4-diamino-5,10-dideaza nonclassical antifolates of formula 3.

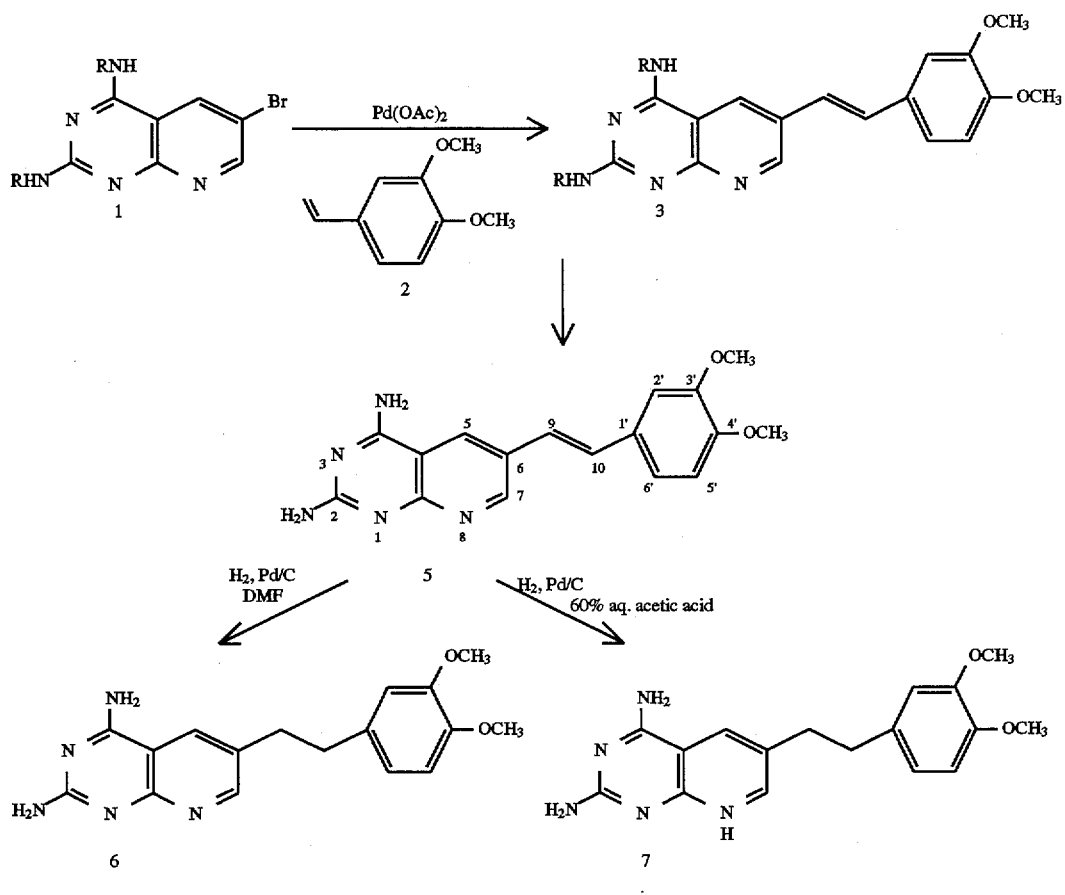

2,4-dipivaloylamino-6-bromopyrido[2,3-d]pyrimidine (1).

To a stirred solution of 10 g (80 mmoles) of 2,4,6-triaminopyrimidine (8) in 15 ml of concentrated hydrochloric acid and 10 ml of absolute ethanol at 80° was added 12.06 g (80 mmoles) of bromomalonaldehyde (9) [24] (freshly prepared). The solution was brought to reflux for 5 minutes, when an orange colored solid falls out of solution. This thick suspension was cooled rapidly to <5° and diluted with water (30 ml). The mixture was basified with concentrated ammonium hydroxide to pH 8, with the temperature maintained at below 10°. The precipitate was filtered, washed with water until neutral, air dried, and further dried in vacuo over phosphorus pentoxide at 70°. To the crude dried precipitate (16.0 g) was added 25 ml of pyridine and 50 ml (240 mmoles) of pivaloyl anhydride. The mixture was refluxed under nitrogen for 8 hours. The reaction mixture was cooled to room temperature, and the excess pyridine and pivaloyl anhydride were removed under reduced pressure (oil-pump). To the dark brown sticky residue was added 500 ml of methylene chloride. The suspension was stirred overnight and the undissolved material filtered. The filtrate was evaporated to ~50 ml and chromatographed on a wet (methylene chloride) silica gel column (2.4×38 cm). The column was eluted with methylene chloride, collecting 10 ml fractions. Fractions showing a single spot on TLC, were pooled and evaporated to afford a white residue which was recrystallized from acetone to give 10.1 g (39%).

2,4-dipivaloylamino-6-[2-(3',4'-dimethoxyphenyl)ethenyl)pyrido[2,3-d]pyrimidine (3).

To a mixture of 1.94 g (6 mmoles) of 11, 15 mg (0.06 mmole, 1% w/w) of palladium acetate, 38 mg (0.12 mmole) of tri-o-tolylphosphine, 7 mg (0.03 mmole) of cuprous iodide and 5 ml of triethylamine was added 30 ml of acetonitrile and the solution brought to reflux under nitrogen. To the solution, under reflux, was added 1.97 g (12 mmoles, 2 equivalents) of 3,4-dimethoxystyrene (2). The progress of the reaction was followed by TLC (silica gel, methylene chloride:methanol, 15:1 v/v) for formation of product ($R_f$=0.56). Following 18 hours of reflux the mixture was cooled to 5°. The precipitate formed was filtered, washed with cold acetonitrile and air dried. The solid was dissolved in a mixture of methylene chloride-methanol, 9:1 (v/v) (~30 ml) and passed through a short column of silica gel (2.4×10 cm), using 10% methanol in methylene chloride as eluent. The eluate was evaporated under reduced pressure to a small volume (~30 ml). This solution was left overnight at 0° to deposit a solid which was filtered, washed with ice-cold methanol and dried to afford 1.55 g (53%) of 1 as a bright orange solid, TLC; silica gel, methylene chloride:methanol, 15:1 (v/v), $R_f$=0.56.

2,4-diamino-6-[2-(3',4'-dimethoxyphenyl)ethenyl]pyrido[2,3-d]pyrimidine (5).

To a solution of 500 mg (1.01 mmoles) of 3 in 15 ml of methylene chloride and 5 ml of methanol was added 40 ml of liquid ammonia. This solution was sealed and stirred in a Parr acid digestion bomb for a period of 66 hours. The liquid ammonia was allowed to evaporate and the suspension filtered. The yellow solid residue was extracted with 100 ml of boiling methanol followed by 100 ml of boiling acetone, and air dried. For purification, the solid was dissolved in 15% aqueous acetic acid and clarified through a thick pad of glass wool. The solution was evaporated under reduced pressure to dryness and the residue stirred overnight in the dark in a mixture of methanol:ethyl acetate, 1:1 (v/v) and filtered. The solid was dried in vacuo at 70° to afford 216 mg of 5 (78%) as a yellowish-orange solid, mp >300°. The compound was homogenous on TLC; (a) cellulose, 50% aqueous acetic acid, $R_f$=0.45, (b) silica gel, chloroform-methanol-ammonium hydroxide, 14:2:1, $R_f$=0.18.

2,4-diamino-6-[2-(3',4'-dimethoxyphenyl)ethyl]pyrido[2,3-d]pyrimidine (6).

In order to increase solubility of 5 in dimethylformamide it was first converted to the triflouroacetate salt. Compound 5, 100 mg (0.3 mmole), was dissolved to dryness (<30°) with an oil pump. The residue was dissolved in 20 ml of dimethylformamide and 200 mg of 5% Pd-C was added to the solution. The suspension was hydrogenated at 25 psi for fifteen minutes in a Parr apparatus. TLC (cellulose, 10% aqueous acetic acid v/v) of the reaction mixture showed two spots, the desired product 6 ($R_f$=0.5) and unreacted 5 ($F_f$=0.01). The reaction mixture was filtered through Celite and the Celite washed with 20 ml of dimethylformamide. The filLrate was evaporated under reduced pressure (<50°) to dryness. The residue was dissolved in 30 ml of methanol-glacial acetic acid (95:5 v/v) mixture. To this solution was added 0.5 g of silica gel, and the solvent was removed under reduced pressure. This solid dispersion was loaded on a dry silica gel column (35 g, 2.4×20 cm). The column was flushed with 500 ml chloroform, and then eluted stepwise with 100 ml portions of 99:1, (v/v) chloroformamethanol to 80:20, (v/v) chloroform-methanol collecting 10 ml fractions. Fractions showing a single spot on TLC corresponding to the product were pooled and evaporated to dryness. (The product elutes in fractions corresponding to 85:15 to 81:19 (v/v) chloroform-methanol). The residue was stirred overnight in ethyl acetate in the dark and filtered. The filtered solid was dried in vacuo at 700 over phosphorus pentoxide to afford 51 mg (51%) of a pale yellow solid, mp >300°. The compound was homogenous on TLC; (a) cellulose, 10% aqueous acetic acid, $R_f$=0.5, (b) silica gel, chloroform-methanol-ammonium hydroxide, 14:2:1, $R_f$=0.22, (c) silica gel, ethyl acetate-methanol, 2:1, $R_f$=0.41.

2,4-diamino-6-[2-(3',4'-dimethoxyphenyl)ethyl]-5,6,7,8-tetrahydro]H-pyrido[2,3-d]pyrimidine (7).

To a solution of 280 mg (0.87 mmole) of 5 in 40 ml of 60% aqueous acetic acid was added 435 mg of 5% Pd-C, and the suspension was hydrogenated in a Parr apparatus at 50 psi for 24 hours. The catalyst was filtered through Celite and washed with 60% aqueous acetic acid. The filtrate and washings were evaporated to dryness under reduced pressure (<35°). The residue was taken up in methanol (20 ml) and dissolved with a drop of glacial acetic acid. To this solution was added 1 g of silica gel and the suspension evaporated under reduced pressure to dryness. This silica gel plug (with product evenly dispersed in it) was loaded on a dry silica gel column (31 g, 2.4×18 cm). The column was first flushed with chloroform (500 ml) and then eluted stepwise with 100 ml portions of 99:1 to 89:11 (v/v) of chloroform-methanol, collecting 10 ml fractions. (The product elutes in fractions corresponding to 93:7 to 90:10 (v/v) chloroform-methanol). Fractions showing a single spot were pooled, filtered through a pad of glass wool and evaporated under reduced pressure to give a residue which was re-evaporated twice with 30 ml portions of diethyl ether. The solid obtained was triturated with anhydrous ether in the dark overnight, filtered and dried in vacuo over phosphorus pentoxide at 70° to give 190 mg (67%) of a white solid, mp 180°–182° dec. The compound was homogenous on TLC in three different solvent systems; (a) cellulose, 10% aqueous acetic acid, $R_f$=0.45, (b) silica gel, chloroform-methanol-ammonium hydroxide, 14:2:1, $R_f$=0.43, (c) silica gel, ethyl acetate-methanol, 2:1, $R_f$=0.45.

EXAMPLE VI

The following are various methods for making the [3,2-d]pyrimidine compounds of FIG. 4.

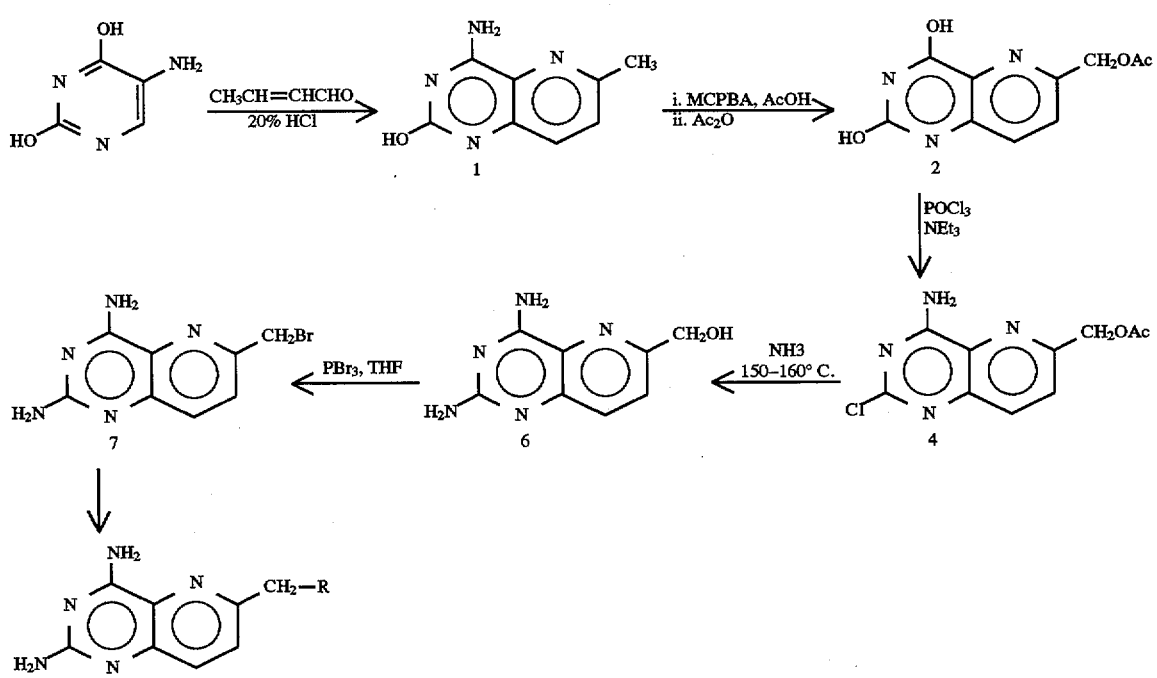

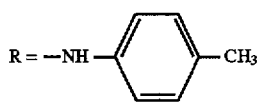

8

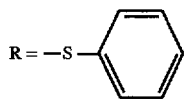

9

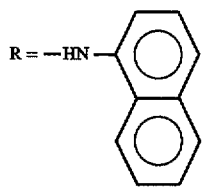

10

2,4-dioxo-6-methylpyrido-[3,2-d]pyrimidine 1.

20 g of 5-aminouracil (40 mmol), 80 ml of 20% HCl and 4 ml of crotonaldehyde (50 mmol) were heated together under reflux for 1 hour. The solution was evaporated to dryness under rotarary evaporation. Water was added to the residue so as to make the mixture just stirtable and then it was triturated with ammonium hydroxide with strong stirring until the pH increased to 10–11. Stirring was continued for another 10 minutes. The precipitate was filtered and was washed with minimal methanol and then chloroform and dried to give 17.58 g (63%) of 1.

6-(Acetoxymethyl)-2,4-dioxopyrido[3,2-d]pyrimidine 2.

1.77 g of 1 (10 mmol) in 50 ml of glacial acetic acid containing 6.5 g of MCPBA (57–85%) was refluxed for 3 hours. Acetic anhydride (40 ml) was added to the hot reaction mixture and the refluxing was continued for another half an hour. The clear brown solution was evaporated to dryness and the solid was stirred with ether (100 ml) and filtered. The solid was crystallized from ethanol to give 1.55 g (66%) of 2.

6-(Acetoxymethyl)-2,4-dichloropyrido[3,2-d]pyrimidine 4.

1.5 g 2 (6.4 mmol) was refluxed with 38 mL of phosphoryl chloride containing 2.5 mL of triethylamine for 8 hours. The volume was reduced to about 5 mL by rotarary evaporation. The dark syrup was poured into crushed ice. The cold suspension was extracted with methylene chloride (3×50 mL) and washed with cold water until the washing were neutral. The organic layer was dried over anhydrous sodium sulfate and evaporated to dryness under rotarary evaporation. The dark solid residue was stirred and refluxed with petroleum ether (30°–60° C.) and suitable amount of de, coloring charcoal, filtered through Celite, which was repeated twice. The combined liquid solution was concentrated until the light yellow solid precipitated out and was allowed to cool to room temperature and stored in refrigerator for 2 hours. The crystallized solid was filtered and dried to give 0.86 g (50%) of 4.

2,4-diamino-6-(hydroxymethyl)pyrido[3,2-d]pyrimidine 6.

2.5 g of 4 (9.2 mmol) was heated with 30 mL of liquid ammonia in a sealed bomb at 150°–170° C. for 18 hours. After cooling to room temperature, the bomb was opened and the liquid ammonia was allowed to evaporate at room temperature. The solid was crystallized from glacial acetic acid and a small amount of water to give 1.24 g (70%) of 6.

2,4-diamino-6-(bromomethyl)pyrido[3,2-d]pyrimidine 7.

A suspension of 0.72 g (3.77 mmol) of 6 in 12 mL dry THF was stirred for 8 hours with 1 mL of phosphorus tribromide. The precipitated solid was filtered, washed with cold 50% THF-Ether, and dried to give 7. Because of the instability, this compound was not purified further. The $^1$HNMR showed that the majority of the solid was the desired compound.

2,4-diamino-6-(paramethoxyanilinylmethyl)pyrido[3,2-d]pyrimidine 8.

To a suspension of 7 (~3.5 mmol, based on the amount of 6 being used) in anhydroUs dimethylacetamide was added 0.92 g anisidine (7.5 mmol) and 1.03 g anhydrous potassium (7.5 mmol). After the suspension was stirred for 2 days, almost all of the 7 disappeared. The $R_f$ value of new spot which was assigned as 8 was 0.32 (in 2:8 methanol:chloroform). The solvent DMAC was removed under diminished pressure. The solid residue was washed with methanol three times and filtered. To the combined liquid was added silica gel and the methanol was evaporated to dryness. Separation to afford pure product was carried out by column chromatography.

2,4-diamino-6-(phenylthiomethyl)pyrido[3,2-d]pyrimidine 9.

To a suspension of 7 (~2.5 mmol) in anhydrous dimethylacetamide was added 1 mL thiophenol (5 mmol) and 690 mg anhydrous potassium (5 mmol). After the suspension was stirred for 3 days, the spot of 7 disappeared from TLC. The $R_f$ value of one of new spots which is assigned as 9 is 0.35 (in 2:8 methanol:chloroform). The solvent DMAC was removed under diminished pressure. The solid residue was washed with methanol three times and filtered. The combined liquid was added silica gel and then the methanol was evaporated to dryness. A small amount of product was separated through a dry column. $^1$HNMR, the product. After crystallization, 5 mg of pure product was obtained.

2,4-diamino-6-(naphathalinylmethyl)pyddo[3,2-d]pyrimidine 10.

The procedure is same as 8. The reaction time is longer (5 days).

2,4-diamino-6-(phenylthiomethyl)pyrido[3,2-d]pyrimidine 9.

To a suspension of 7 (~5 mmol) in 20 mL anhydrous dimethylacetamide was added 2 mL anisidine (10 mmol) and 1.38 g anhydrous potassium carbonate (10 mmol). After the suspension was stirred for 2 days, the spot of 7 disappeared from TLC. The solvent DMAC was removed under diminished pressure. The solid residue was stirred with 50 mL water for 10 minutes. Then the suspension was extracted with 3×70 mL chloroform. It was found that almost no desired compound appeared in water phase (TLC). The gel-state material between the two phases was collected separately and then added 70% chloroform solvent in methanol to effect solution. The resulting semi-transparent solution was washed with saturated sodium chloride solution. The combined organic phase was concentrated to ~100 mL to which silica gel was added. The solvent was removed to dryness and the residue was dried in the oven for 3 hours (60° C.) and loaded onto a column and separated. The desired pure compound was a white colored compound ($R_f$ value is identical to the former data).

EXAMPLE VII

The following is a method of making the quinazoline compounds of formula 5.

10-Thia-5,8-dideazapteroic acid (10). A suspension of compound 9 (1.82 g, 5 mmol) in 120 mL of 0.2N NaOH was stirred at ambient temperature for 45 hours. Traces of insoluble material were removed by filtration, and the pH of the filtrate was adjusted to 6 with concentrated HCl. The product was isolated by centrifugation and washed with 3×40 mL of $H_2O$. After drying, there was obtained 1.2 g (73%) of white crystalline powder: mp 339°–341° C. dec; TLC, $R_f$=0.58.

Di-tert-butyl 10-thia-5,8-dideazafolate (12). To a suspension of 10 (0.2 g, 0.6 mmol) in 10 mL of DMF were added di-tert-butyl L-glutamate hydrochloride, 11 (0.195 g, 0.66 mmol), and diethyl phosphorocyanidate (0.108 g, 0.66 mmol) in 1.0 mL of DMF. The suspension was treated with 0.134 g (1.32 mmol) of $Et_3N$ in 2 mL of DMF, and the resulting mixture was stirred under $N_2$ at ambient temperature for 1.5 hours. It was then poured into a mixture of EtOAc-$C_6H_6$ (3:1) and the organic layer washed successively with 50 mL of $H_2O$, 60 mL of saturated aqueous $Na_2CO_3$, 50 mL of $H_2O$, and 60 mL of saturated NACl. After drying over $MgSO_4$, the solvent was removed under

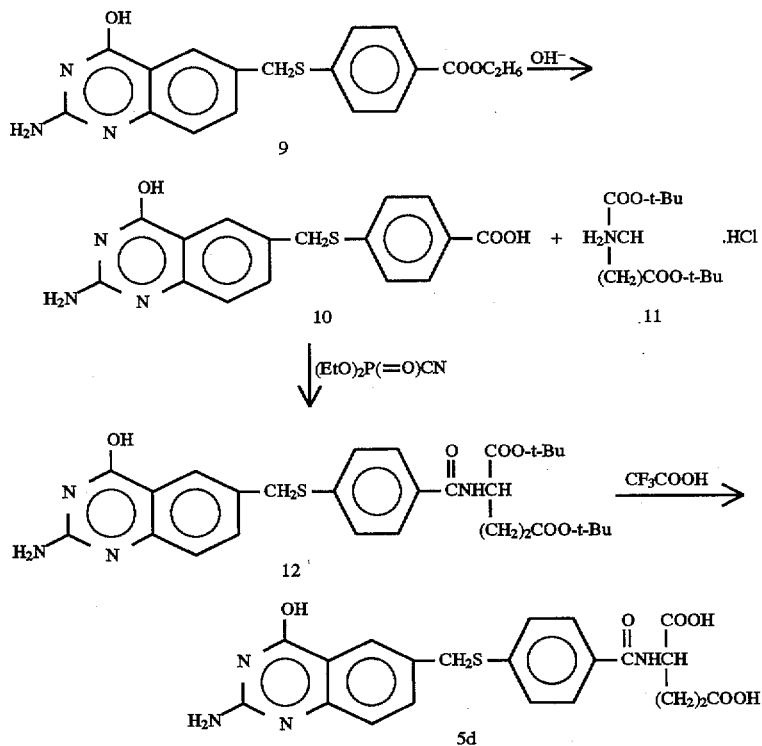

Ethyl 10-thia-5,8-dideazapteroate (9). A solution of 2.7 g (7.5 mmol) of diethyl 4,4'-dithiobisbenzoate in 100 mL of EtOH was reduced with 0.95 g (10 mmol) of $NaBH_4$ at ambient temperature. This was added portionwise to a suspension of 3.8 g (15 mmol) of 2-amino-6-(bromomethyl) -4-hydroxyquinazoline (7) in 20 mL of DMF, and the resulting mixture was stirred at ambient temperature for 18 hours. A negative active halogen test was obtained, indicating that 7 had been consumed, and the EtOH was removed under reduced pressure. The addition of 550 mL of $H_2O$ gave a precipitate, which was separated by filtration and washed with $H_2O$. After recrystallization from DMF-$H_2O$, there was obtained 4.74 g (89%) of white crystalline solid: mp 268° C. dec; TLC, $R_f$=0.33 ($CHCl_3$-MeOH, 7:3).

vacuum. The crude product was applied to a silica gel column and eluted with $CHCl_3$-MeOH, 9:1. Fractions homogeneous by TLC were pooled and evaporated to obtain an off-white powder, which was recrystallized from $CHCl_3$-n-hexane, 1:3. The precipitate was separated by centrifugation to yield 0.27 g (81%) of crystalline white powder: mp 190°–192° C.; TLC, $R_f$=0.79 ($CHCl_3$-MeOH, 4:1).

10-Thia-5,8-dideazafolic Acid (5d). Compound 12 (0.217 g, 0.40 mmol) was dissolved in $CF_3COOH$ (10 mL). After the reaction mixture was stirred under $N_2$ at ambient temperature for 1 hour, the solution was separated under reduced pressure. The yellow oily residue was treated with 40 mL of $Et_2O$ and the off-white precipitate was separated by centrifugation and washed with 3×30 mL of $Et_2O$. The crude product was dissolved in 30 mL of $H_2O$ and the resulting white suspension was basified to pH 11 with 1N NaOH. Traces of insoluble material were removed by filtration, and the tiltrate was brought to pH 3.5 with 1N HCL. The white precipitate was separated by centrifugation, washed three times with $H_2O$, and dried under vacuum at 80° C. for 6 hours, yielding 0.138 g (79%) of white crystalline powder: mp 224°–225° C.; TLC, $R_f$=0.62; HPLC, 34.6 min.

EXAMPLE VIII

The following is a method of making the compounds of formula 6.

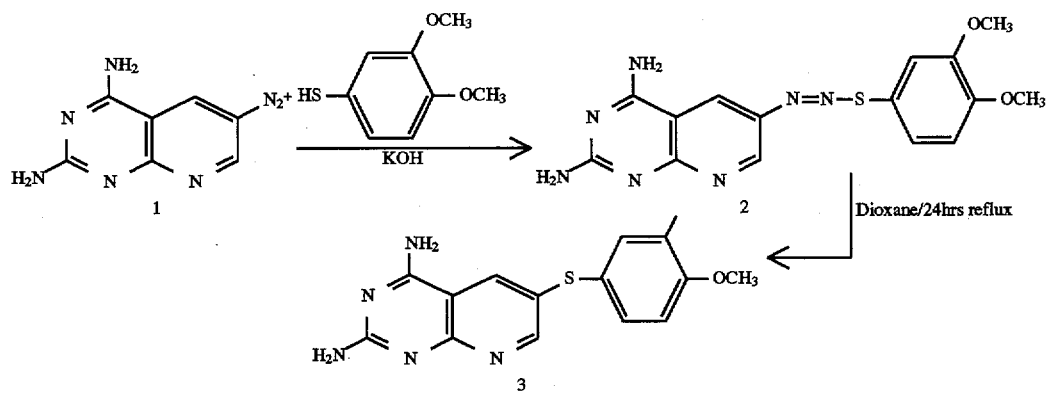

Scheme III

A small scale reaction is conducted to obtain 3',4'-diOMePh analogue of target compound 1. The 6-$NH_2$ analogue was diazotized with $NaNO_2$/HCl at 0° C. over a period of 20 minutes to afford a diazonium salt which was filtered, dissolved in $H_2O$ and added dropwise at 40° C. to an aqueous solution of 3,4-dimethoxybenzene thiol and KOH in order to afford the diaryl sulfide according to the Ziegler reaction. The resulting precipitate was cooled, acidified to pH 4 (gl. AcOH) filtered and basified to pH 8 to afford 136 in 75% yield. Heating 2 in dioxane for 24 hours at reflux affords a product which has the required mass for 3 from mass spectral analysis.

It will be appreciate by those skilled in the art that this invention provides compounds and pharmaceutically acceptable salts thereof effective against infections caused by *Pneumocystis carinii* and *Toxoplasmosis gondii*, a method of preparing these compounds, and a method of using these compounds in a patient for therapeutic or prophylactic purposes.

Whereas, particular embodiments of this invention have been described above for purposes of illustration, it will be evident to those skilled in the art that numerous variations of the details of the present invention may be made without departing from the invention as defined in the appended claims.

We claim:

1. A compound and pharmaceutically acceptable salts having the species formula (4)

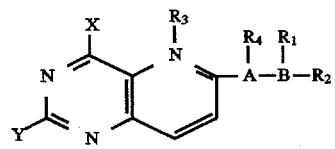

(4)

wherein X and Y may be the same or different and are selected from the group consisting of OH and $NH_2$, wherein A is selected from the group consisting of nitrogen, CH and sulfur and B equals CH when A is selected from the group consisting of sulfur, CH and nitrogen or B equals nitrogen when A equals CH or B equals sulfur when A equals CH wherein $R_3$ is zero; wherein $R_4$ is one of either a hydrogen or a first lower alkyl group except where A equals sulfur wherein $R_4$ equals zero; wherein $R_1$ is selected from the group consisting of hydrogen, a nitroso group, a formyl group, a second lower alkyl group which is the same or different than the first lower alkyl group except when B is equal to sulfur, wherein $R_1$ is equal to zero; and wherein $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alicyclic hydrocarbon group, an alkyltriaryl group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group and a halogen.

2. The compound and pharmaceutically acceptable salts of claim 1 wherein said first lower alkyl group has one to about six carbon atoms branched, unbranched and alicyclic, said second lower alkyl group has one to about six carbon atoms branched, unbranched and alicyclic and said third lower alkyl group has one to about six carbon atoms branched, unbranched and alicyclic; wherein said alkylaryl group is selected from the group consisting of an alkylphenyl and alkylbenzyl group; wherein said alkyldiaryl group is selected from the group consisting of alkylnaphthyl, alkylbenzothiophene, alkylindene, alkylbenzofuran, alkylindole, and alkylaminoquinoline; wherein alkyltriaryl group is an alkylanthracyl group; wherein said substituted aryl group, diaryl group and triaryl group is selected from the group consisting of a mono-, di- and tri-substituted aryl group, diaryl group and triaryl group; wherein said substituted alkylaryl group is selected from the group consisting of mono-, di- and tri-substituted alkylphenyl and alkylbenzyl group; wherein each substituted alkyldiaryl and alkyltriaryl group is selected from the group consisting of a mono-, di- and tri-substituted alkylnaphthyl, alkylbenzothiophene, alkylindole, alkylbenzofuran, alkylindine, alkylaminoquinoline and alkylanthracyl group and wherein each substituent is the same or different and is selected from the group consisting of methyl, ethyl, n-propyl, n-butyl, cyclopropyl, cyclobutyl, cyclopentyl, cyclohexyl, methoxy group, chlorine atom, bromine atom and fluorine atom.

3. The compound and pharmaceutically acceptable salts of claim 1 wherein X and Y are each $NH_2$, $R_1$ is zero, $R_2$ is 2',5'-dimethoxyphenyl, $R_3$ is zero, $R_4$ is hydrogen, A is CH and B is sulfur.

4. The compound and pharmaceutically acceptable salts of claim 1 wherein X and Y are each $NH_2$, $R_1$ is hydrogen, $R_2$ is 2',5'-dimethoxyphenyl, $R_3$ is zero, $R_4$ is $CH_3$, A is nitrogen and B is CH.

5. The compound and pharmaceutically acceptable salts of claim 1 wherein X and Y are each $NH_2$, $R_1$ is hydrogen, $R_2$ is 3',4',5'-trimethoxyphenyl, $R_3$ is zero, $R_4$ is hydrogen, A is CH and B is CH.

6. The compound and pharmaceutically acceptable salts of claim 1 wherein X and Y are each $NH_2$, $R_1$ is hydrogen, $R_2$ is 1'naphthyl, $R_3$ is zero, $R_4$ is hydrogen, A is nitrogen and B is CH.

7. A method of therapeutically treating a patient for an illness consisting of employing a compound and pharmaceutically acceptable salts thereof having the species formula (4)

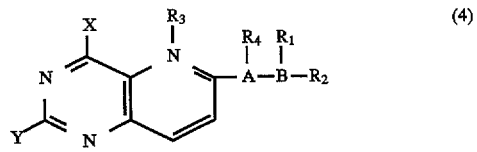

wherein X and Y may be the same or different and are selected from the group consisting of OH and $NH_2$, wherein A is selected from the group consisting of nitrogen, CH and sulfur and B equals CH when A is selected from the group consisting of sulfur, CH and nitrogen or B equals nitrogen when A equals CH or B equals sulfur when A equals CH wherein $R_3$ is zero; wherein $R_4$ is one of either a hydrogen or a first lower alkyl group except where A equals sulfur wherein $R_4$ equals zero; wherein $R_1$ is selected from the group consisting of hydrogen, a nitroso group, a formyl group, a second lower alkyl group which is the same or different than the first lower alkyl group except when B is equal to sulfur, wherein $R_1$ is equal to zero; and wherein $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, an alicyclic hydrocarbon group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group and a halogen;

which comprises:
incorporating said compound in a suitable pharmaceutical carrier;
administering a therapeutically effective amount of said compound incorporated in said carrier to a patient who is immunocompromised; and
employing said method in therapeutically treating a patient for an illness selected from the group consisting of infection by *Pneumocystis carinii* and *Toxoplasmosis gondii*.

8. The method of claim 7 including employing said carrier selected from the group consisting of physiologic saline and 5% dextrose for injection.

9. The method of claim 7 including administering said compound incorporated in said carrier to a patient by the parenteral route.

10. The method of claim 7 including administering said compound incorporated in said carrier to a patient by the oral route.

11. The method of claim 7 including administering said compound incorporated in said carrier to a patient topically.

12. A method of prophylactically administering to a patient a compound and pharmaceutically acceptable salt thereof having the species formula (4)

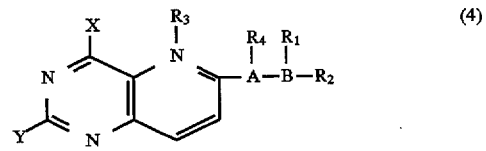

wherein X and Y may be the same or different and are selected from the group consisting of OH and $NH_2$ wherein A is selected from the group consisting of nitrogen, CH and sulfur and B equals CH when A is selected from the group consisting of sulfur, CH and nitrogen or B equals nitrogen when A equals CH or B equals sulfur when A equals CH wherein $R_3$ is zero; wherein $R_4$ is one of either a hydrogen or a first lower alkyl group except where A equals sulfur wherein $R_4$ equals zero; wherein $R_1$ is selected from the group consisting of hydrogen, a nitroso group, a formyl group, a second lower alkyl group which is the same or different than the first lower alkyl group except when B is equal to sulfur, wherein $R_1$ is equal to zero; and wherein $R_2$ is selected from the group consisting of a third lower alkyl group which is the same or different than the first lower alkyl group and the second lower alkyl group, an aryl group, an alkylaryl group, a substituted aryl group, a substituted alkylaryl group, a diaryl group, a triaryl group, an alkyldiaryl group, an alkyltriaryl group, an alicyclic hydrocarbon group, a substituted diaryl group, and a substituted triaryl group, and each substituent of the substituted aryl group, diaryl group, triaryl group, or the substituted alkylaryl group, alkyldiaryl group, alkyltriaryl group is the same or different and is selected from the group consisting of a fourth lower alkyl group which is the same as or different than the first lower alkyl group, the second lower alkyl group, the third lower alkyl group, an alkoxy, a substituted alkoxyaryloxy group and a halogen;

which comprises:
incorporating said compound in a suitable pharmaceutical carrier;
administering a prophylactically effective amount of said compound incorporated in said carrier to a patient who is immunocompromised; and
employing said method in prophylactically treating a patient to provide protection against an illness selected a group consisting of infection by *Pneumocystis carinii* and *Toxoplasmosis gondii*.

13. The method of claim 12 including employing said carrier selected from the group consisting of physiologic saline and 5% dextrose for injection.

14. The method of claim 12 including administering said compound incorporated in said carrier to a patient by the parenteral route.

15. The method of claim 12 including administering said compound incorporated in said carrier to a patient by the oral route.

16. The method of claim 12 including administering said compound incorporated in said carrier to a patient topically.

* * * * *

UNITED STATES PATENT AND TRADEMARK OFFICE
CERTIFICATE OF CORRECTION

PATENT NO. : 5,736,547

DATED : April 7, 1998

INVENTOR(S) : Aleem Gangjee

It is certified that errors appear in the above-identified patent and that said Letters Patent should be corrected as shown below:

In the Abstract "nitrogan" should read --nitrogen-- as originally submitted.

Col. 2, line 5 "Dam" should read, --Data--, as originally submitted.

Col. 2, line 16, "pyfidimine" should read --pyridimine-- as originally submitted.

Col. 2, line 67, "aikoxy" should read --alkoxy-- as originally submitted.

Col. 4, line 36, "alkyI" should read --alkyl-- as originally submitted.

Col. 8, line 51, add a --;-- between sulfur B.

Col. 10, line 38, remove the "." between alkyl group.

Col. 10, line 41, remove the "-" between alk yltriaryl, should read --alkyltriaryl-- as originally submitted.

Col. 11, line 64 "alkylanthraeyl" should read --alkylanthracyl-- as originally submitted.

Col. 12, line 6 "ethantale" should read --ethantate-- as originally submitted.

Col. 12, line 38 "immunecompromised" should read --immunocompromised-- as originally submitted.

Col. 13, line 12 "diehlorophenyl" should read --dichlorophenyl-- as originally submitted.

Col. 14, line 9 "2-fiuorobenzyl" should read --2-fluorobenzyl-- as originally submitted.

UNITED STATES PATENT AND TRADEMARK OFFICE
CERTIFICATE OF CORRECTION

PATENT NO. : 5,736,547

DATED : April 7, 1998

INVENTOR(S) : Aleem Gangjee

It is certified that errors appear in the above-identified patent and that said Letters Patent should be corrected as shown below:

Col. 14, line 9 "difiuorobenzyl" should read –difluorobenzyl—as originally submitted.

Col. 14, line 10 "difiuorobenzyl" should read –difluorobenzyl—in 2 instances as originally submitted.

Col. 16, line 30 "leucovodn" should read –leucovorin—as originally submitted.

Col. 16, line 35 "pcDI-IFR" should read –pcDHFR—as originally submitted.

Col. 17, line 42 "fn:st" should read –first—as originally submitted.

Col. 20, line 5, "flitrate" should read –filtrate—as originally submitted.

Col. 20, line 14, remove the "o" between 4 diaminopyrido.

Col. 21, line 1 "diaminopyddo" should read –diaminopyrido—as originally submitted.

Col. 21, line 37 the "2" should be a –1—as originally submitted.

Col. 21, line 40 the symbol "$NO_2$" should read –$NH_2$—as originally submitted.

Col. 24, line 47 "flitrate" should read –filtrate—as originally submitted.

Col. 25, line 57 "flltrate" should read –filtrate— as originally submitted.

UNITED STATES PATENT AND TRADEMARK OFFICE
CERTIFICATE OF CORRECTION

PATENT NO. : 5,736,547

DATED : April 7, 1998

INVENTOR(S) :
Aleem Gangjee

It is certified that error appears in the above-identified patent and that said Letters Patent is hereby corrected as shown below:

Col. 32, second equation, last compound, "
$$\begin{array}{c} \text{COO-t-Bu} \\ | \\ \text{H}_2\text{NCH} \quad\quad .\text{HCl} \\ | \\ \text{(CH}_2\text{)COO-t-Bu} \\ 11 \end{array}$$
" should read $$--\begin{array}{c} \text{COO-t-Bu} \\ | \\ \text{H}_2\text{NCH} \quad\quad \cdot\text{HCl} \\ | \\ \text{(CH}_2\text{)}_2\text{COO-t-Bu} \\ 11 \end{array}--$$

Col. 33, line 3, "tiltrate" should read --filtrate-- as originally submitted.

Col. 35, line 5, the first "$R_2$" should read --$R_1$--.

UNITED STATES PATENT AND TRADEMARK OFFICE
CERTIFICATE OF CORRECTION

PATENT NO. : 5,736,547

DATED : April 7, 1998

INVENTOR(S) : Aleem Gangjee

It is certified that error appears in the above-identified patent and that said Letters Patent is hereby corrected as shown below:

Col. 27, line 20 "filLrate" should read —filtrate— as originally submitted.

Col. 27, line 34 "700" should read —70°— as originally submitted.

Col. 27, Example VI, 3$^{rd}$ equation "NH$_2$" should read —OH— as originally submitted.

Col. 29, line 53 remove the "." and insert a -- - -- after "de" as originally submitted.

Col. 30, line 59 "pyddo" should read —pyrido— as originally submitted.

Signed and Sealed this

Twenty-second Day of August, 2000

Attest:

Q. TODD DICKINSON

Attesting Officer          Director of Patents and Trademarks